(12) United States Patent
Johnson et al.

(10) Patent No.: US 7,503,929 B2
(45) Date of Patent: Mar. 17, 2009

(54) PROSTHETIC HEART VALVE SYSTEM

(75) Inventors: Keith M. Johnson, Champlin, MN (US); Jack D. Lemmon, St. Louis Park, MN (US); Joseph C. Morrow, Eden Prairie, MN (US); Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 325 days.

(21) Appl. No.: 11/337,422

(22) Filed: Jan. 23, 2006

(65) Prior Publication Data

US 2006/0235510 A1    Oct. 19, 2006

Related U.S. Application Data

(63) Continuation of application No. 10/336,622, filed on Jan. 2, 2003, now Pat. No. 7,033,390.

(60) Provisional application No. 60/345,297, filed on Jan. 2, 2002.

(51) Int. Cl.
    *A61F 2/24*    (2006.01)
(52) U.S. Cl. .................................... 623/2.11
(58) Field of Classification Search .......... 623/2.1–2.19
    See application file for complete search history.

(56) References Cited

U.S. PATENT DOCUMENTS

| 3,099,016 | A | 7/1963 | Edwards |
| 3,197,788 | A | 8/1965 | Segger |
| 3,263,239 | A | 8/1966 | Edwards et al. |
| 3,365,728 | A | 1/1968 | Edwards et al. |
| 3,466,671 | A | 9/1969 | Siposs |
| 3,509,582 | A | 5/1970 | Pierie |
| 3,534,410 | A | 10/1970 | Raible |
| 3,570,014 | A | 3/1971 | Hancock |

(Continued)

FOREIGN PATENT DOCUMENTS

EP    0084395    8/1986

(Continued)

OTHER PUBLICATIONS

U.S. Appl. No. 60/117,445, filed Jan. 26, 1999, Carpentier et al.

(Continued)

*Primary Examiner*—Suzette J Gherbi
(74) *Attorney, Agent, or Firm*—Mike Jaro; Jeffrey J. Hohenshell

(57) ABSTRACT

A prosthetic heart valve system including a prosthetic heart valve and a deflection device. The deflection device includes a line and a connector assembly including a tensioning component. The line interconnects and passes through free ends of stent posts associated with the heart valve, and is further connected to the tensioning component. The tensioning component is transitionable to a tensioning state in which the line is tensioned to inwardly deflect the stent posts. In this regard, the tensioning component is self-locking relative to the line in the tensioning state, and an entirety of the line extending distal the tensioning device does not extend beyond a stent portion of the heart valve opposite the stent posts. In a preferred embodiment, a holder body is further included, coupled to the heart valve apart from the deflection device.

34 Claims, 21 Drawing Sheets

U.S. PATENT DOCUMENTS

| | | |
|---|---|---|
| 3,656,185 A | 4/1972 | Carpentier |
| 3,710,744 A | 1/1973 | Goodenough et al. |
| 3,714,671 A | 2/1973 | Edwards et al. |
| 3,723,996 A | 4/1973 | Raible et al. |
| 3,755,823 A | 9/1973 | Hancock |
| 4,084,268 A | 4/1978 | Ionescu et al. |
| 4,106,129 A | 8/1978 | Carpentier et al. |
| 4,259,753 A | 4/1981 | Liotta et al. |
| 4,291,420 A | 9/1981 | Reul |
| 4,297,749 A | 11/1981 | Davis et al. |
| 4,343,048 A | 8/1982 | Ross et al. |
| 4,388,735 A | 6/1983 | Ionescu et al. |
| 4,451,936 A | 6/1984 | Carpentier et al. |
| 4,470,157 A | 9/1984 | Love |
| 4,501,030 A | 2/1985 | Lane |
| 4,626,255 A | 12/1986 | Reichart et al. |
| 4,629,459 A | 12/1986 | Ionescu et al. |
| 4,725,274 A | 2/1988 | Lane et al. |
| 4,778,461 A | 10/1988 | Pietsch et al. |
| 4,851,000 A | 7/1989 | Gupta |
| 4,865,600 A | 9/1989 | Carpentier et al. |
| 5,147,391 A | 9/1992 | Lane |
| 5,163,953 A | 11/1992 | Vince |
| 5,163,955 A | 11/1992 | Love et al. |
| 5,258,023 A | 11/1993 | Reger |
| 5,411,552 A | 5/1995 | Andersen et al. |
| 5,449,384 A | 9/1995 | Johnson |
| 5,476,510 A | 12/1995 | Eberhardt et al. |
| 5,489,297 A | 2/1996 | Duran |
| 5,489,298 A | 2/1996 | Love et al. |
| 5,500,016 A | 3/1996 | Fisher |
| 5,549,665 A | 8/1996 | Vesely et al. |
| 5,554,185 A | 9/1996 | Block et al. |
| 5,697,382 A | 12/1997 | Love et al. |
| 5,702,368 A | 12/1997 | Stevens et al. |
| 5,716,401 A | 2/1998 | Eberhardt et al. |
| 5,716,417 A | 2/1998 | Girard et al. |
| 5,728,152 A | 3/1998 | Mirsch, II et al. |
| 5,800,527 A | 9/1998 | Jansen et al. |
| 5,800,531 A | 9/1998 | Cosgrove et al. |
| 5,855,601 A | 1/1999 | Bessler et al. |
| 5,861,028 A | 1/1999 | Angell |
| 5,895,420 A | 4/1999 | Mirsch, II et al. |
| 5,928,281 A | 7/1999 | Huynh et al. |
| 5,935,163 A | 8/1999 | Gabbay |
| 5,964,770 A | 10/1999 | Flomenblit et al. |
| 6,019,790 A | 2/2000 | Holmberg et al. |
| 6,074,419 A | 6/2000 | Healy et al. |
| 6,102,845 A | 8/2000 | Woodard et al. |
| 6,338,740 B1 | 1/2002 | Carpentier |
| 6,409,758 B2 | 6/2002 | Stobie et al. |
| 6,558,418 B2 | 5/2003 | Carpentier et al. |
| 6,702,852 B2 | 3/2004 | Stobie et al. |
| 6,719,785 B2 | 4/2004 | Schoon et al. |
| 6,736,845 B2 | 5/2004 | Marquez et al. |
| 6,964,682 B2 | 11/2005 | Nguyen-Thien-Nhon et al. |
| 6,966,925 B2 | 11/2005 | Stobie |
| 7,033,390 B2 * | 4/2006 | Johnson et al. ............ 623/2.11 |
| 2002/0082686 A1 * | 6/2002 | Nguyen-Thien-Nhon et al. ........ 623/2.11 |
| 2003/0125805 A1 | 7/2003 | Johnson et al. |
| 2004/0024451 A1 | 2/2004 | Johnson et al. |
| 2004/0059413 A1 | 3/2004 | Argento |
| 2004/0138741 A1 | 7/2004 | Stobie et al. |
| 2004/0148017 A1 * | 7/2004 | Stobie ....................... 623/2.11 |
| 2004/0148018 A1 | 7/2004 | Carpentier et al. |

FOREIGN PATENT DOCUMENTS

| | | |
|---|---|---|
| EP | 0515324 | 12/1996 |
| GB | 2011259 A | 7/1979 |
| GB | 2108393 | 5/1983 |
| GB | 2279134 | 12/1994 |
| RU | 1806696 | 4/1993 |
| WO | 90/11738 | 10/1990 |
| WO | 92/12690 | 8/1992 |
| WO | 93/18721 | 9/1993 |
| WO | 95/28899 | 11/1995 |
| WO | 97/46177 | 12/1997 |
| WO | 98/43556 | 10/1998 |
| WO | 00/64382 | 4/1999 |
| WO | 00/00107 | 1/2000 |
| WO | 00/42950 | 7/2000 |
| WO | 00/67661 | 11/2000 |
| WO | 02/49545 | 6/2002 |

OTHER PUBLICATIONS

Bernhard et al., "A 'Semi-Supported' Porcine Xenograft—Description and First Clinical Use," Thorac. Cardiovas. Surgeon 37 (1989) pp. 313-315.

Krucinski et al., "Numerical Simulation of Leaflet Flexure in Bioprosthetic Valves Mounted on Rigid and Expansile Stents," J. Biomechanics, vol. 26, No. 8 (1993) pp. 929-943.

Jansen et al., "New J-3 flexible-leaflet polyurethane heart valve prosthesis with improved hydrodynamic performance," International Journal of Artificial Organs, vol. 14 No. 10 (1991) pp. 655-660.

Wright JM et al., Hancock II—An Improved Bioprosthesis. In: Cohn LJ, Galucci V. ed. Cardiac Bioprosthesis. New York, NY: New York Medical Books, 1982.

Hancock® II Bioprosthesis, Clinical Compendium, Copyright 2003, Medtronic, Inc.

Bortolotti et al., "Porcine Valve Durability: A Comparison Between Hancock Standard and Hancock II Bioprostheses," Ann Thorac Surg 60:S216-20 (1995).

John S. T. Masterson, Robert T. Miyigashia, Peter Allen, A Ian Munro and William G. Trapp, Universal Cardiac Valve Holder; Annal. Thor. Surgery, Apr. 1977, p. 376.

Grismer et al., "A Suture Holder and Separator Attachment to the Starr-Edwards Prosthetic Valve Holders," Surgery, Gynecology and Obstetrics, Mar. 1965, pp. 583-584.

\* cited by examiner

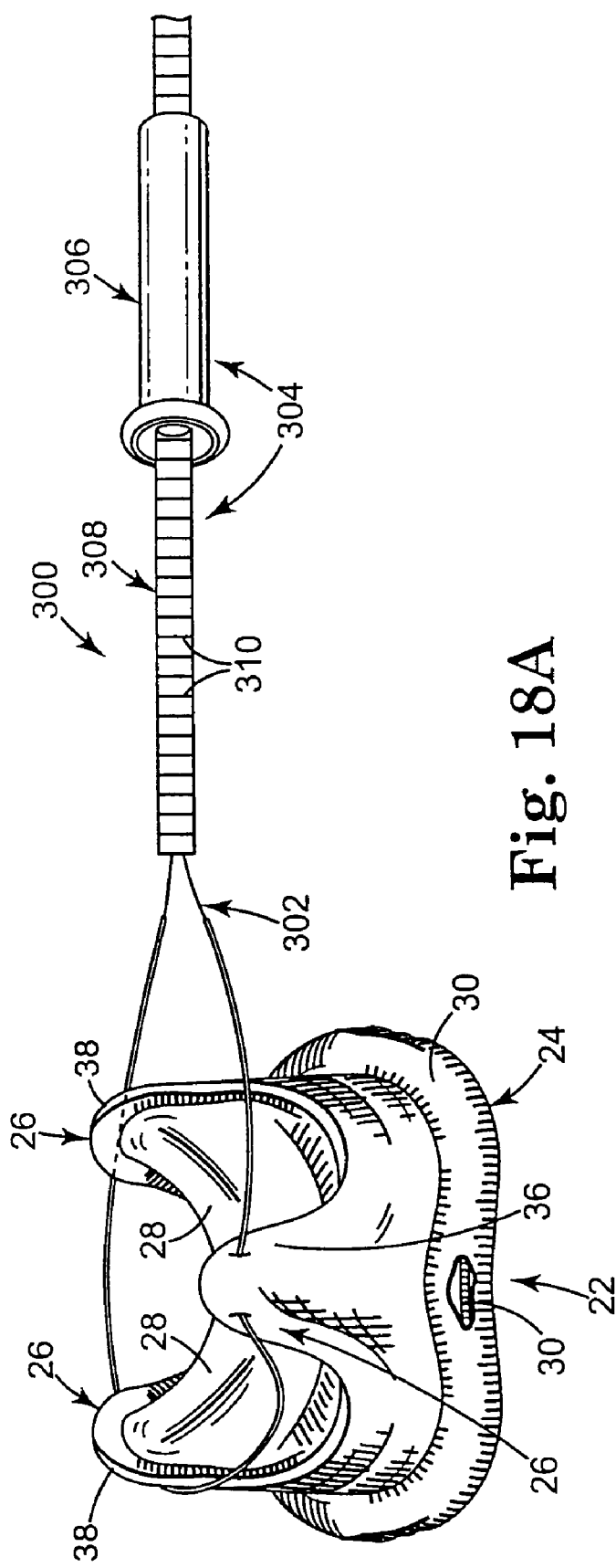
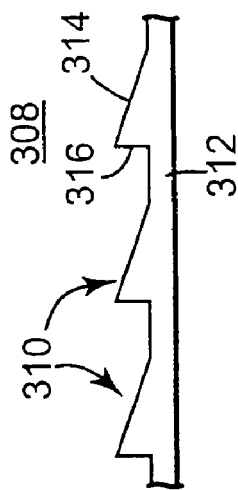
Fig. 18A
Fig. 18B

PROSTHETIC HEART VALVE SYSTEM

CROSS-REFERENCE TO RELATED APPLICATIONS

This application is a continuation of U.S. patent application Ser. No. 10/336,622 filed Jan. 2, 2003, now U.S. Pat. No. 7,033,390 that claims priority to, and is entitled to the benefit of, U.S. Provisional Patent Application Ser. No. 60/345,297, filed Jan. 2, 2002, and U.S. patent application Ser. No. 10/131,933, filed Apr. 25, 2002, the teachings of all of which are incorporated herein by reference.

BACKGROUND OF THE INVENTION

The present invention relates to implantable prosthetic heart valves with flexible leaflets. More particularly, it relates to a prosthetic heart valve system including a device for effectuating prosthetic heart valve stent post deflection during implantation thereof.

Various types and configurations of prosthetic heart valves, used to replace diseased natural human heart valves, are known in the art. The actual shape and configuration of any particular prosthetic heart valve is, of course, dependent to some extent upon the valve being replaced (i.e., mitral valve, tricuspid valve, aortic valve, and pulmonary valve). In general terms, however, the prosthetic heart valve design attempts to replicate the function of the valve being replaced and thus will include valve leaflet-like structures. With this in mind, prosthetic heart valves are generally classified as either forming relatively rigid leaflets and those forming relative flexible leaflets.

As used throughout this specification a "prosthetic heart valves having relatively flexible leaflets" (or "prosthetic heart valve") encompass bioprosthetic heart valves having leaflets made of a biological material as well as synthetic heart valves having leaflets made of a synthetic (e.g., polymeric) material. Regardless, prosthetic heart valves are generally categorized as having a frame or stent, and those which have no stent. The stent in a stented prosthetic heart valve normally includes a substantially circular base (or stent ring), around which an annular suture material is disposed for suturing the prosthesis to heart tissue. Further, stent forms at least two, typically three, support structures extending from the stent ring. The support structures are commonly referred to as stent posts or commissure posts and include an internal, rigid yet flexible structure extending from the stent ring, covered by a cloth-like material similar to that of the annular suture material. The stent or commissure posts define the juncture between adjacent tissue or synthetic leaflets otherwise secured thereto. Examples of bioprosthetic heart valves are described in U.S. Pat. No. 4,106,129 to Carpentier et al., and U.S. Pat. No. 5,037,434 to Lane, the teachings of which are incorporated herein by reference. These disclosures detail a conventional configuration of three leaflets wherein one leaflet is disposed between each pair of stent or commissure posts.

Implantation of a prosthetic heart valve presents numerous technical challenges, regardless of the prosthesis' configuration. With respect to stented prosthetic heart valves, inventive efforts have focused on minimizing the complications associated with mitral valve replacement. In this regard, a prosthetic mitral valve is normally implanted by placing the prosthesis into the mitral valve annulus with the stent posts projecting blindly deep into the patient's left ventricle. Due to a lack of visibility through the prosthetic valve, a surgeon can inadvertently loop sutures around the stent posts during suturing of the annular suture ring portion of the prosthesis. Similarly, the extending stent posts may undesirably "snag" on chordae or trabeculae inside the left ventricular cavity. To avoid these complications, various prosthetic valve holders have been designed that inwardly retract or deflect and hold the mitral prosthetic stent posts during implantation. In general terms, available prosthetic mitral heart valve holders include an elongated handle and a holder mechanism. The holder mechanism is secured to the stent ring and adapted to inwardly deflect the stent posts upon rotation of the handle. In this regard, the handle extends proximally from the holder mechanism, opposite the stent posts. An exemplary prosthetic mitral heart valve holder is described in U.S. Pat. No. 4,865,600 to Carpentier et al.

Medtronic Hancock® mitral valves are available mounted to a holder providing a mechanism for inward deflection, as illustrated in the brochures: "A New Dimension—The Hancock II Bioprosthesis," Medtronic Inc., 1991, publication number UC8903226EN and "A New Light on the Hancock Bioprosthesis," Medtronic Inc., 1988, publication number UC8801713EN, both incorporated herein by reference in their entireties. This holder includes a ratcheting spool, mounted below the sewing ring, which when rotated by means of an attached handle, pulls lengths of suture inward, in turn pulling sutures extending upward though the commissure posts and between the commissure posts downward, to deflect the commissure posts inward.

The above-described prosthetic mitral heart valve holder devices are well-suited for mitral valve replacement. In general terms, the mitral valve surgical site is relatively easily accessed, with minimal anatomical obstructions "above" or away from the implant site. Thus, the surgeon is afforded a large, unobstructed area for locating and maneuvering the handle as well as performing necessary procedural steps (e.g., suturing the annulus suture ring to the heart tissue) with minimal or no interference from the handle and/or mechanism. This mitral valve implant site characteristic allows the currently available prosthetic mitral valve holder to assume a relatively bulky and complex form.

Aortic prosthetic heart valve implantation presents certain constraints distinct from those associated with mitral valve replacement. In particular, with aortic heart valve implantation, a surgeon is often faced with little room to maneuver. Depending upon the type of aortotomy performed, the surgeon may first have to pass the prosthesis through a restriction in the aorta known as the sinotubular junction, which is often times smaller than the tissue annulus onto which the prosthetic heart valve will be sutured. The surgeon must then "seat" the prosthetic heart valve securely in or on the tissue annulus with downward pressure. The surgeon must then tie down all annular sutures (via knots), ensuring that a hemostatic seal is made. Finally, the surgeon must cut-off all sutures in close proximity to the knots. Relative to the orientation of the aortic prosthetic heart valve during the implant procedure, the stent posts extend proximally toward the surgeon (as opposed to the distal stent post direction associated with mitral valve replacement). Thus, while the concern for "snagging" of the stent posts (i.e., inadvertently looping sutures about stent post is minimal during aortic prosthetic heart valve implantation, the proximally extending stent posts associated with the stented prosthesis interfere with the various other maneuvers required of the surgeon.

In light of the above, it would be desirable to inwardly deflect the stent posts during implantation of the aortic prosthetic heart valve. Unfortunately, the above-described mitral prosthetic heart valve holders are of little value for aortic valve replacement procedures in that the holder positions the handle to extend in a direction opposite that of the stent posts.

As such, the handle would have to be removed in order to implant the aortic prosthetic heart valve. Without this handle component, the holder cannot be operated to inwardly deflect the stent posts. Attempts have been made to correct this incompatibility by reconfiguring the holder to extend the handle in the same direction as the stent posts, as described, for example, in U.S. Pat. Nos. 5,476,510 and 5,716,410, both to Eberhardt et al., the teachings of which are incorporated herein by reference.

More recently, a few surgeons have begun to employ a self-fashioned technique to approximate (i.e., inwardly deflect) stent posts of an aortic prosthetic heart valve. The technique entails threading a suture through the cover material otherwise covering the stent posts. A surgical tube is slidably placed over the suture and is then forced toward the prosthetic heart valve, causing the stent posts to inwardly deflect. A surgical clamp is then used to temporarily lock the tube along the suture, theoretically maintaining the stent posts in an approximate position. Unfortunately, it is impossible for the surgeon to know or otherwise confirm the degree to which the stent posts have deflected. To this end, the prosthetic heart valve can be damaged if the stent posts are overly deflected and/or maintained in an overtly deflected position for an extended period. The valve can also be damaged by the surgeon if cutting sutures are used or the suture needle employed to thread the suture through the stent posts is inappropriately passed through critical stress areas of the valve, leading to premature valve failure. Further, the above technique continues to require an elongated component (surgical clamp) that impedes convenient handling/implant of the prosthetic heart valve. Thus, this makeshift approach is not optimal.

Devices for assisting in the implantation of stented prosthetic heart valves are essentially limited to mitral valve replacement procedures. These stent posts deflection apparatuses are relatively bulky and mechanically complex. Conversely, rudimentary techniques improvised by some surgeons are unreliable and may lead to prosthesis damage. Therefore, a need exists for a preassembled stent post deflection device that is safe, simple in form and operation, and appropriate for any heart valve location, including the aortic heart valve.

SUMMARY OF THE INVENTION

One aspect of the present invention relates prosthetic heart valve system including a prosthetic heart valve and a deflection device. The prosthetic heart valve includes a stent and a plurality of stent posts extending from the stent. Each of the stent posts defines a free end. The deflection device includes a line and a connector assembly including a tensioning component. The line interconnects and passes through the free ends of the stent posts, and is further connected to the tensioning component. The tensioning component is transitionable to a tensioning state in which the line is tensioned to inwardly deflect the stent posts. In this regard, the tensioning component is self-locking relative to the line in the tensioning state, and an entirety of the line extending distal the tensioning device does not extend beyond the stent opposite the free ends of the stent posts.

Another aspect of the present invention relates to a prosthetic heart valve system including a prosthetic heart valve, a deflection device, and a holder. The deflection device includes a tensioning component coupled to the prosthetic heart valve, preferably by a line. The holder includes a holder body coupled to the prosthetic heart valve, preferably by at least a second line. In this regard, the tensioning component and the holder body are separately coupled to the prosthetic heart valve such that the holder body can be removed from the prosthetic heart valve without affecting coupling between the tensioning device and the prosthetic heart valve.

BRIEF DESCRIPTION OF THE DRAWINGS

FIG. 18A is a perspective view of another alternative embodiment deflection device in accordance with the present invention;

FIG. 18B is an enlarged side view of a portion of the deflection device of FIG. 18A;

DESCRIPTION OF THE PREFERRED EMBODIMENTS

Figure 1:
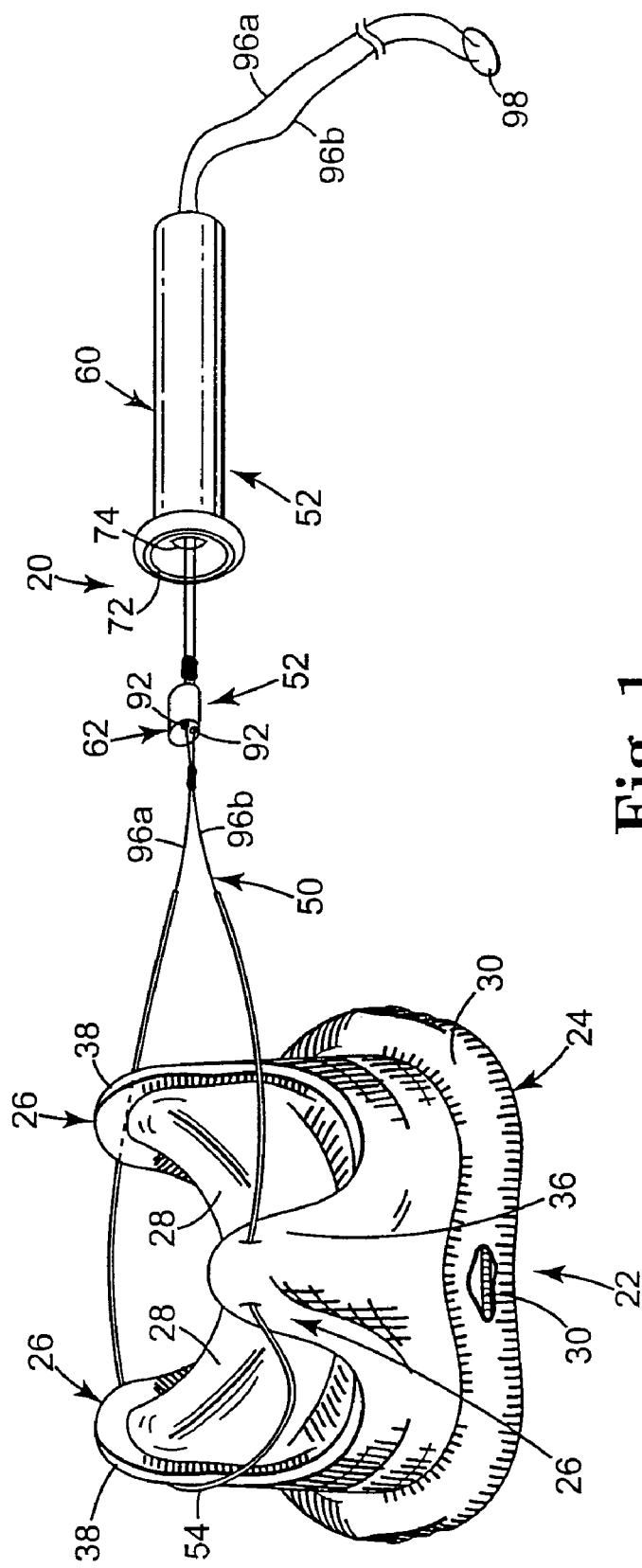
FIG. 1 is a perspective view of a first embodiment deflection device in accordance with the present invention coupled to a prosthetic heart valve.

One preferred embodiment of a deflection device 20 in combination with a prosthetic heart valve 22 is shown in FIG. 1. As a point of reference, the prosthetic heart valve 22 can assume a wide variety of forms (e.g., bioprosthetic heart valve having tissue leaflets or a synthetic heart valve having polymeric leaflets), and can be specifically configured for replacing any heart valve. In general terms, however, the prosthetic heart valve 22 includes a stent 24, forming stent posts 26, and leaflets 28. As is known in the art, the stent 24 provides a support framework for the prosthetic heart valve 22 and further includes an inner frame member or stent ring 30 (shown partially in FIG. 1) encompassed by a cover 32 that otherwise serves as a sewing or suturing annulus or flange. The stent posts 26 extend from the stent ring 30, and each are preferably composed of an internal frame structure (not shown) encompassed by a cloth covering 36. Each of the stent posts 26 terminates in a free end 38 opposite the stent ring 30. As is known in the art, the internal structure of each of the stent posts 26 is formed of a stiff but resiliently bendable material. This construction allows the stent posts 26 to be deflected from the orientation shown in FIG. 1 (e.g., the respective free ends 38 deflected inwardly) by an external force. Once this external force is removed, however, the stent posts 26 return to the form of FIG. 1. Finally, the covering 36 is preferably formed of a fabric material to which the leaflets 28 are sutured. It will be understood that above-described prosthetic heart valve 22 is but one acceptable configuration. For example, more or less than three of the stent posts 26 can be provided, the stent posts 26 may incorporate a different covering 36 and/or eliminate the covering 36.

With the above-description of the prosthetic heart valve 22 in mind, the deflection device 20 includes a line 50 and a connector assembly 52. Details on the various components are provided below. In general terms, and upon final assembly to the prosthetic heart valve 22, the line 50 extends between and interconnects the free ends 38 of the stent posts 26. The connector assembly 52 is connected to the line 50 proximal the prosthetic heart valve 22. In this regard, the connector assembly 52 is transitionable from an unlocked state (illustrated in FIG. 1) to a self-actuating locked state in which the line 50 is locked relative to the connector assembly 52. In this regard, a predetermined length of the line 50 extends distal the connector assembly 52 in the locked state for deflecting the stent posts 26 as part of an implant procedure.

The line 50 is preferably a monofilament suture, but alternatively can be any other type of suture material, string, rope, wire, polymer strip, etc. In one preferred embodiment where the stent posts 26 include the covering 36, the line 50 is a suture that passes through (e.g., stitched) the respective free end 38 coverings 36. Alternatively, other attachment techniques are equally applicable. For example, the prosthetic heart valve 22 can be constructed such that a line-receiving component (e.g., a small tube) is provided at each stent posts 26 that readily slidably receive the line 50. Preferably, however, the line 50 is configured to maintain its structural integrity when subjected to a tension force, such that the line 50 can effectuate inward deflection of the stent posts 26 as described in greater detail below. In this regard, the connector assembly 52 is coupled to the line 50 such that the line 50 defines a loop 54 (referenced generally in FIG. 1) that interconnects the stent posts 26. A length of the loop 54 is dictated by an orientation or state of the connector assembly 52, and can be shortened (or tensioned) to effectuate deflection of the stent posts 26.

In one preferred embodiment, the connector assembly 52 consists of a housing or tensioning component 60 and a locking element 62. In general terms, the housing 60 is slidably connected to the line 50, whereas the locking element 62 is affixed to the line 50. That is to say, relative to the unlocked state of FIG. 1, a position of the locking element 62 relative to the line 50, and in particular the loop 54, will not change, whereas the housing 60 is slidable along the line 50. With this configuration, the housing 60 can be slid in a distal fashion (relative to the arrangement of FIG. 1) along the line 50, whereby the locking element 60 is received within the housing 60. As at least a distal portion of the housing 60 is distally moved beyond the locking element 62, the housing 60 tensions the line 50, and in particular the loop 54, causing the stent posts 26 to inwardly deflect.

Figure 2A:
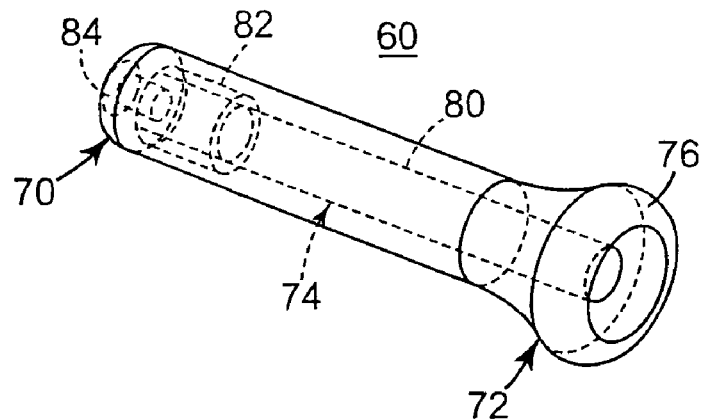
FIG. 2A is an enlarged, perspective view of a housing portion of the deflection device of FIG. 1.
Figure 2B:
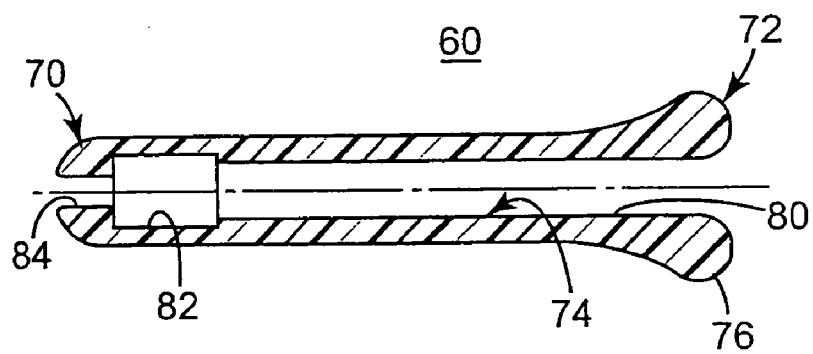
FIG. 2B is a longitudinal cross-sectional view of the housing of FIG. 2A.
Figure 2C:
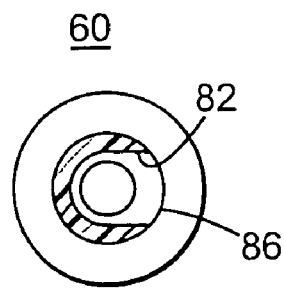
FIG. 2C is a transverse cross-sectional view of the housing of FIG. 2A.

The housing 60 is shown in greater detail in FIGS. 2A-2C. In general terms, the housing 60 is a tubular body and defines a proximal end 70, a distal end 72, and a central passage 74. The central passage 74 is sized to slidably receive the line 50 (FIG. 1). Further, as described below, the central passage 74 is configured to receive the locking element 62 (FIG. 1) at the distal end 72, and retain the locking element 62 adjacent the proximal end 70.

An outer surface of the housing 60 at the distal end 72 preferably forms a flange 76. As best shown in FIG. 2B, the flange 76 is rounded at the central passage 74 so as to minimize damage to the line 50 as the housing 60 is slid along a length thereof, as well as to guide the locking element 62 into the central passage 74 during use.

The central passage 74 includes a distal section 80, a cavity 82, and a proximal section 84. The distal section 80 is sized in accordance with the locking element 62 (FIG. 1). That is to say, a diameter or outer dimension of the distal section 80 is sized to slidably receive the locking element 62. In one preferred embodiment, the distal section 80 has a diameter in the range of 0.05 0.09 inch (1.3-2.3 mm), more preferably 0.7 inch (1.8 mm), although other dimensions are equally acceptable. Regardless, the distal section 80 preferably assumes a uniform diameter or outer dimension, that is only slightly larger than that of the locking element 62. In this way, the locking element 62 will not overtly rotate or otherwise deflect within the distal section 80. Instead, the housing 60 uniformly slides over and along the locking element 62 along the distal section 80.

The cavity 82 is configured to receive and maintain the locking element 62 (FIG. 1), and thus is sized in accordance with the locking element 62. As shown in FIG. 2B, the cavity 82 defines an outer diameter or dimension greater than that defined by the distal section 80. As described in greater detail below, the locking element 62 is preferably configured to slightly rotate or pivot upon entering the cavity 82, such as via interaction with the line 50 (FIG. 1). With this slight rotation, the locking element 62 is then retained or "locked" within the cavity 82. Thus, the cavity 82 defines an axial length slightly greater than that of the locking element 62, for example in one preferred embodiment in the range of 0.09-0.15 inch (2.3-3.8 mm), more preferably 0.12 inch (3.0 mm). Similarly, the cavity 82 preferably defines an outer diameter greater than that of the locking element 62, for example in one preferred embodiment in the range of 0.065-0.125 inch (1.65-3.175 mm), more preferably 0.095 inch (2.41 mm). Alternatively, other dimensions are equally acceptable. Regardless, the housing or tensioning component 60 is self-locking relative to the line; no auxiliary tools, such as a surgical clamp, are required to lock the housing 60 relative to the line 50.

Finally, the proximal section 84 defines an outer diameter or dimension smaller than that of the locking element 62. With this configuration, then, as the housing 60 is slid in a distal fashion over the locking element 62, the locking element 62 is prevented from passing through the proximal section 84.

The housing 60 is preferably an integrally formed component, comprised of a stiff, biocompatible material such as acetal. Alternatively, other materials such as nylon, polypropylene, polysulfone, titanium, stainless steel, etc., are equally acceptable. As described in greater detail below, the housing 60 is preferably configured to permanently retain the locking element 62 (FIG. 1) within the cavity 82. That is to say, once the locking element 62 is "locked" within the cavity 82, a user is not afforded the ability to disengage the locking element 62 therefrom. Alternatively, however, the housing 60 can be configured to allow for selective disengagement of the locking element 62 from the cavity 82. For example, the housing 60 can be formed of two or more parts that can be disassembled from one another. With this configuration, disassembly of the housing parts allows for removal of the locking element 62. Alternatively, and with reference to FIG. 2C, the housing 60 can form the cavity 82 so as to be radially accessible through a passage 86 in an exterior of the housing 60. With this configuration, a surgeon can simply maneuver the locking element 62 via the passage 86 so as to disengage the locking element 62 from the cavity 82.

Figure 3A:
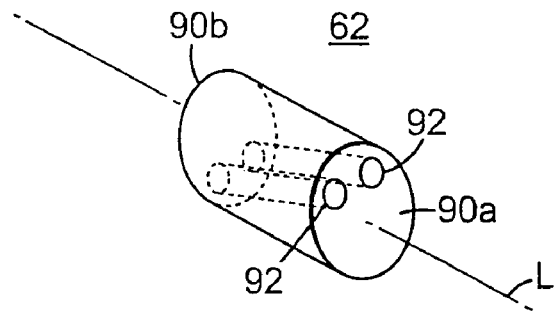
FIG. 3A is an enlarged, perspective view of a locking element portion of the deflection device of FIG. 1.
Figure 3B:
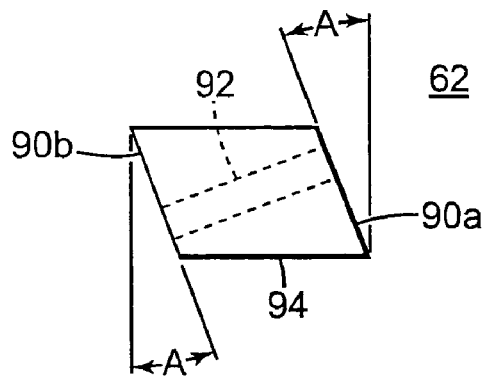
FIG. 3B is a longitudinal cross-sectional view of the locking element of FIG. 3A.
Figure 3C:
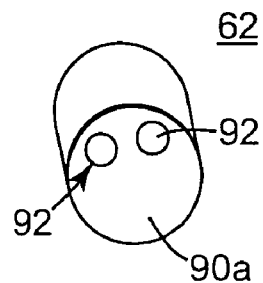
FIG. 3C is an end view of the locking element of FIG. 3A.

The locking element 62 is shown in greater detail in FIGS. 3A-3C. In general terms, the locking element 62 is preferably a cylindrical body or bead defining opposing ends 90a, 90b, a longitudinal axis L and bores 92. The bores 92 extend between the opposing ends 90a, 90b, and are sized to slidably receive the line 50 (FIG. 1). In one preferred embodiment, two of the bores 92 are provided. Regardless, and as best shown in FIG. 3B, the bores 92 extend in a non-parallel fashion relative to the longitudinal axis L. In other words, the bores 92 are formed to extend in an oblique offset fashion relative to the longitudinal axis L. Similarly, the opposing ends 90a, 90b are preferably not perpendicular relative to the longitudinal axis L. That is to say, relative to a longitudinal sidewall 94 defined by the locking element 62 (the longitudinal sidewall 94 being parallel with the longitudinal axis L), the respective opposing ends 90a, 90b extend at an angle A in the range of 10-30°, more preferably 20°. Preferably, however, the bores 92 are perpendicular relative to the opposing ends 90a, 90b.

The locking element 62 is preferably integrally formed from a rigid, biocompatible material such as acetal. Alternatively, other materials such as nylon, polypropylene, polysulfone, titanium, stainless steel, etc., are equally acceptable. Regardless, the locking element 62 is sized in accordance with the central passage 74 (FIG. 2A) of the housing 60 (FIG. 1) as previously described. Thus, in one preferred embodiment, the locking element 62 has an outer diameter or dimension in the range of 0.05-0.07 inch (1.3-1.8 mm), more preferably 0.061 inch (1.55 mm). Further, the locking element preferably has an overall length in the range of 0.08-0.14 inch (2.0-3.6 mm), more preferably 0.11 inch (2.8 mm). Of course, other dimensions corresponding with those of the central passage 74 are equally acceptable.

Returning to FIG. 1, the deflection device 20 is preferably assembled to the prosthetic heart valve 22 substantially as follows. As a point of reference, the one preferred assembly technique is provided for an aortic prosthetic heart valve. While the deflection device 20 can be assembled in a similar fashion to other types of prosthetic heart valves, slightly varying techniques can be employed (e.g., for a mitral prosthetic heart valve as described elsewhere). The line 50 is first connected to the stent posts 26 as shown. In one preferred embodiment, the line 50 is passed through (e.g., stitched) the stent post coverings 36 adjacent the respective free ends 38. Once stitched, the line 50 effectively forms the loop 54, with opposing sides 96a, 96b extending proximally from the prosthetic valve 22. The line 50 can be secured to prosthetic heart valve 22 such that the sides 96a, 96b extend from adjacent stent post 26 as shown, or can be positioned such that the sides 96a, 96b extend, from the same stent post 26.

The locking element 62 is then secured to the line 50, with the opposing sides 96a, 96b extending through respective ones of the bores 92. In this regard, the locking element 62 is secured to the line 50 at a fixed and predetermined location. More particularly, the locking element 62 is specifically located so that a predetermined length of the line 50 extends distal the locking element 62, with the predetermined length being dictated by a configuration of the housing 60, as described below. In this regard, the locking element 62 can be secured to the line 50 in a number of different fashions, for example by forming knots in the line 50 proximal and distal the locking element 62. Regardless, in the unlocked state of FIG. 1, a length of the loop 54 is defined by a position of the locking element 62. In this unlocked state, the loop 54 is of sufficient length so as to not be tensioned about the stent posts 26. In other words, in the unlocked state, the loop 54 does not cause the stent posts 26 to inwardly deflect.

The housing 60 is then slidably received over the line 50 proximal the locking element 62. As shown in FIG. 1, the line 50 continues to form the opposing sides 96a, 96b proximal the locking element 62. The opposing sides 96a, 96b are slidably received within the central passage 74 of the housing 60. Where desired, a retention device 98 can be secured to the opposing sides 96a, 96b proximal the housing 60 so as to prevent accidental removal the housing 60 from the line 50. Regardless, following assembly of the deflection device 20 to the prosthetic heart valve 22, the combination prosthetic heart valve 22/deflection device 20 can be presented to a surgeon as a singular implantation kit or prosthetic heart valve system.

Figure 4:
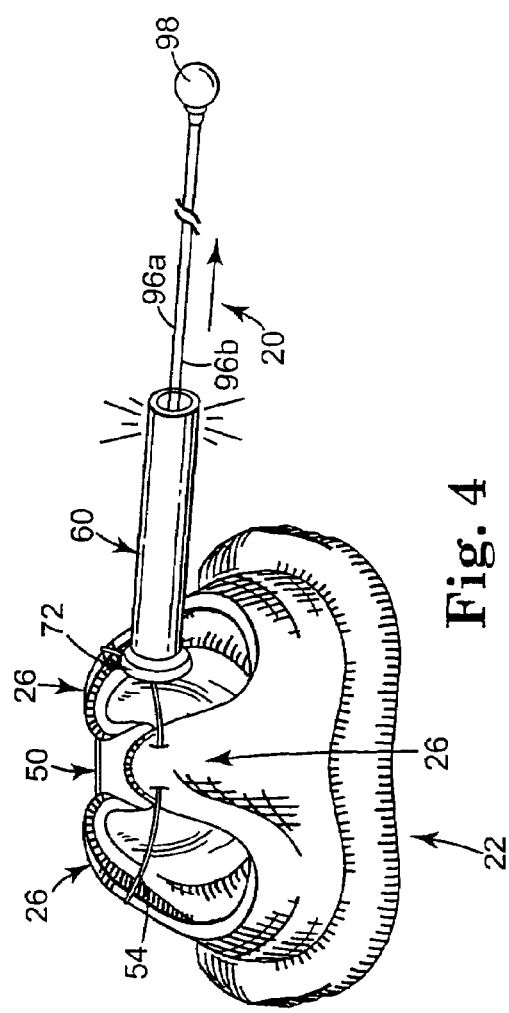
FIG. 4 is a cross-sectional view of a portion of the deflection device of FIG. 1 in a locked state.

During use, the deflection device 20 is initially in the unlocked state of FIG. 1, whereby the stent posts 26 are not inwardly deflected. Following known surgical procedures by which access to the implant site is gained, the deflection device 20 is transitioned to a locked state as shown in FIG. 4. In particular, and with additional reference to FIG. 1, the housing 60 is slid along the line 50 in a distal fashion. To assist in this maneuver, the surgeon (not shown) preferably grasps the line 50 proximal the housing 60, and pulls the line 50 taut. Distal movement of the housing 60 continues until the distal end 72 of the housing 60 is adjacent the locking element 62. With additional distal movement, the locking element 62 enters the central passage 74 of the housing 60 at the distal end 72 thereof. As previously described, the central passage 74, and in particular the distal section 80 (FIG. 2B), is sized such that the locking element 62 can be slidably received within the central passage 74, but will not overtly pivot or rotate relative to the longitudinal axis L (FIG. 3A).

Figure 5:
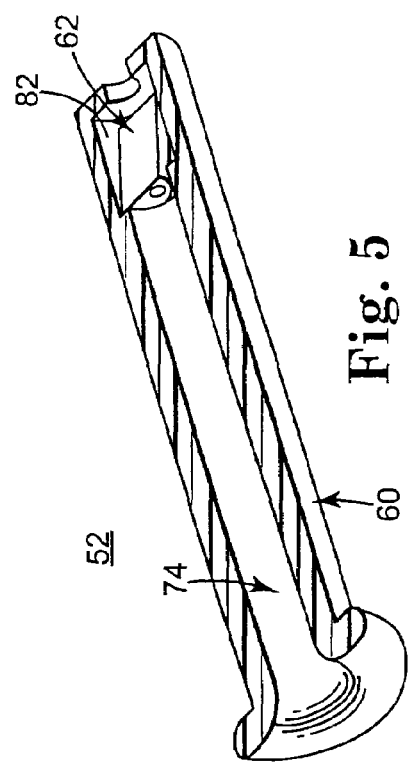
FIG. 5 illustrates use of the deflection device of FIG. 1 in conjunction with a prosthetic heart valve.

Distal movement of the housing 60 continues, with the locking element 62 sliding within the central passage 74. In this regard, as the distal end 72 extends distal the locking element 62, the housing 60 decreases a length of the loop 54, imparting a tension thereon. As a length of the loop 54 decreases, the loop 54 tensions the stent posts 26, causing the stent posts 26 to inwardly deflect. This inward deflection continues with further distal movement of the housing 60 until the locking element 62 is received within the cavity 82 (FIG. 2A) of the housing 60. The locking element 62 will rotate or "catch" within the cavity 82 due to an axial torque being placed on the locking element 62 via the tensioned line 50 passing through the locking element 62 in a plane that is not parallel with the longitudinal axis L (or the sidewall 94 (FIG. 3C)). The locking element 62 is effectively captured within the cavity 82, thereby preventing further tension-causing distal movement of the housing 60. This relationship is illustrated by the perspective, cross-sectional view of FIG. 5 in which the connector assembly 52 is shown in the locked state.

In a preferred embodiment, the locking element 62 is positioned along the line 50 at a predetermined location that provides a predetermined or desired inward deflection of the stent posts 26. In particular, a location of the locking element 62 relative to the line 50, and in particular the loop 54, is based upon a length of the housing 60 distal the cavity 82 (FIG. 2B). Once again, in the locked state, the distal end 72 of the housing 60 dictates a length of the loop 54 and thus the extent of inward deflection of the stent post 26. The locking element 62 is fixed to the line 50 such that the connector assembly 50 assumes the locked position or state whereby the distal end 72 of the housing 60 has reduced a length of the loop 54 to a desired extent. Thus, the locking element 62 is located such that the loop 54 is sufficiently large so as to not cause inward deflection of the stent posts 26, yet positions the housing 60 in the locked state at a point whereby a length of the loop 54 has reduced a predetermined amount to cause and maintain a desired amount or extent of inward deflection of the stent posts 26.

Regardless of a location of the locking element 62, transition or movement of the housing 60 continues until a tensioning state is achieved in which tensioning of the line 50 causes inward deflection of the stent posts 26. In this tensioning state, an entirety of the line 50 extending distal the housing or tensioning component 60 (e.g., the loop 54 in FIG. 4) does not extend beyond the stent 24 opposite the free ends 38. That is to say, relative to the orientation of FIG. 4, the tensioning section 54 of the line 50 does not extend below the stent 24, thereby minimizing possible complications during implantation.

In one preferred embodiment, the materials selected for the housing 60 and the locking element 62 are such that an audible noise or "click" is produced as the locking element 62 transitions to the locked state. Upon hearing this noise, the surgeon will know that the locked state has been achieved, and will not attempt to further slide the housing 60 while tensioning the line 50 proximal thereof. Alternatively, or in addition, a visible marker can be placed along the line 50 corresponding with the housing 60 having reached the locked state. For example, a color marking can be provided along the line 50 proximal the locking element 62 at a distance approximating a length of the housing 60 between the cavity 82 (FIG. 2A) and the proximal end 70. With this configuration, the marking will be "exposed" relative to the proximal end 70 once the housing 60 has been advanced to the locked state. Notably, adapting the deflection device to provide an audible or visual confirmation of the locked state is not a necessary feature of the present invention.

With the deflection device 20 in the locked state, and thus with the stent posts 26 inwardly deflected, the prosthetic heart valve 22 is implanted in accordance with known procedures (e.g., sutured to heart tissue). Once the prosthetic heart valve 22 has been secured at the desired location, the deflection device 20 is then released from the prosthetic heart valve 22. In accordance with one preferred embodiment, the locking element 62 is permanently locked within the housing 60 in the locked state. As such, removal of the deflection device 20 entails cutting the line 50 distal the connector assembly 52 (i.e., distal the housing 60 in the locked state). Alternatively, the connector assembly 52 can be configured to allow the locking element 62 to be manually disengaged from the housing 60 as previously described.

The above-described deflection device 20 is easy to use, and consistently provides desired stent post deflection. In this regard, the prosthetic heart valve 22 will typically have a known acceptable stent posts deflection range or maximum. The deflection device 20 can be assembled to the prosthetic heart valve 22 so as to ensure that the manufactured deflection tolerance is not exceeded. In other words, and as previously described, the known distal extension of the housing 60 relative to the locking element 62 in the locked state is known, and thus the resulting tension or length reduction of the loop 54 is also known. Based upon the desired or acceptable stent posts deflection value, a length of the loop 54 necessary to achieve this extent of deflection can be determined. Subsequently, the connector assembly 52 can then be assembled to the line 50 so as to achieve this same loop length in the locked state. In an alternative embodiment, the deflection device 20 preferably further includes temporary locking components (not shown) provided along the line 50 that interact with the housing 60 in a manner similar to that previously described, but are adapted to not be permanently locked to the housing 60. These temporary locking components can assume a variety of forms (e.g., knots, discrete components, etc.), and are positioned proximal locking element 62. More particularly, the temporary locking elements allow a surgeon to effectuate a slight deflection of the stent posts 26 (i.e., maintaining a lesser degree of deflection than otherwise associated with the final locked state provided by a position of the locking element 62); however, because the housing 60 is not permanently locked to the temporary locking elements, the housing 60 can be further advanced or retracted by the surgeon as desired.

Figure 6A:
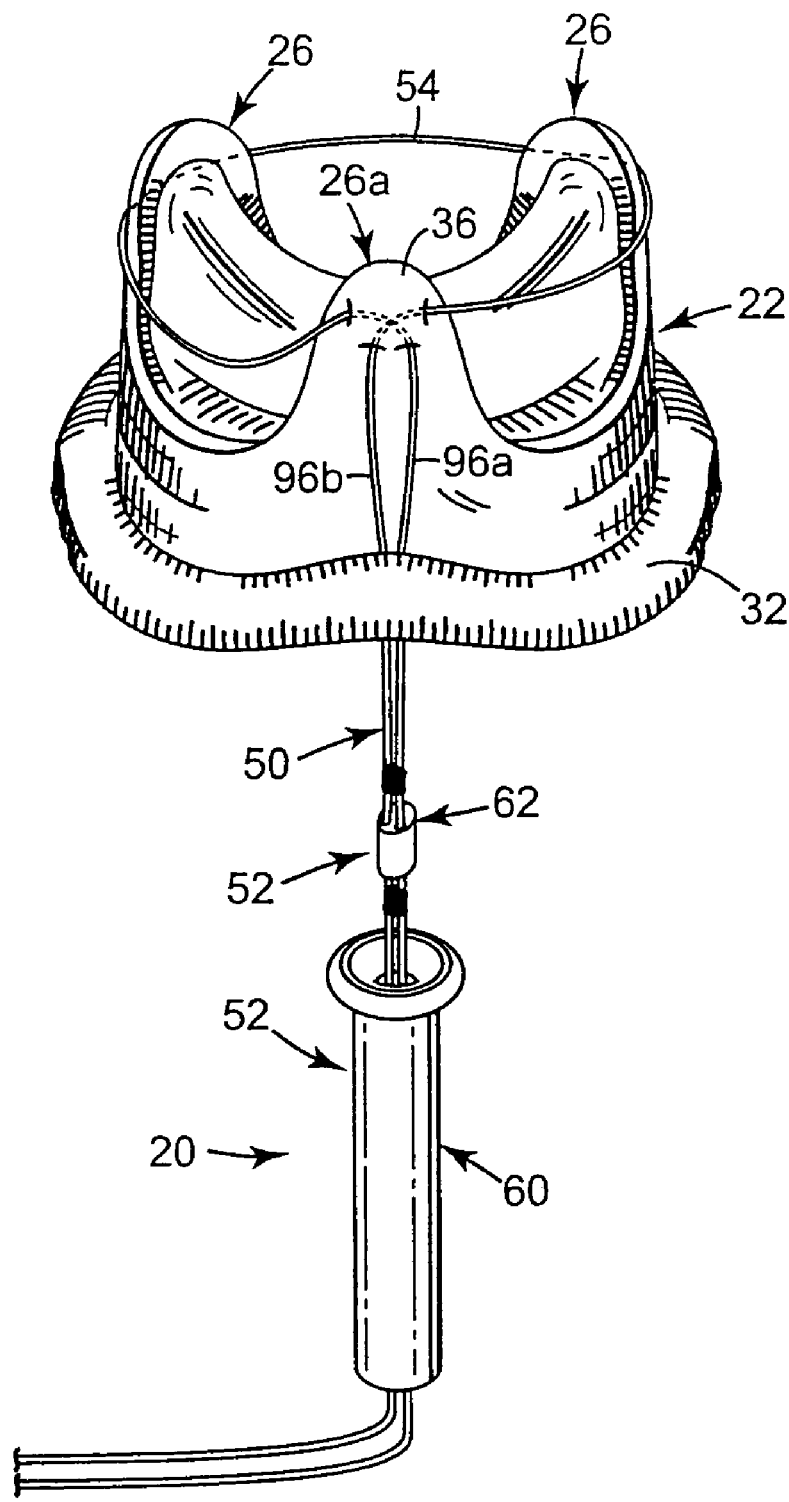
FIGS. 6A-6B illustrate the deflection device of FIG. 1 assembled to an alternative prosthetic heart valve.

As previously indicated, the above-described deflection device 20 assembly technique is preferably utilized in conjunction with an aortic prosthetic heart valve. This technique is preferably slightly altered where the prosthetic heart valve 22 is a mitral prosthetic heart valve. In this regard, FIG. 6A illustrates the deflection device 20 assembled to the prosthetic heart valve 22 in a manner conducive to mitral valve replacement. As a starting point, implantation of a mitral prosthetic heart valve generally entails placement of the stent posts 26 within the patient's left ventricle. In other words, the typical mitral prosthetic heart valve implantation procedure orients the prosthetic heart valve 22 such that the stent posts 26 extend away from (or distal) the surgeon. This is opposite the orientation normally utilized with an aortic heart valve replacement. With this in mind, assembly of the deflection device 20 again begins with connection of the line 50 to the stent posts 26. This interconnection forms the loop 54. However, unlike the assembly technique previously described for an aortic prosthetic heart valve (e.g., FIG. 1), the opposing sides 96a, 96b of the line 50 preferably cross over one another within the covering 36 associated with one of the stent posts (designated as the stent post 26a). Further, shown with FIG. 6A, the opposing sides 96a, 96b are directed downwardly (relative to the orientation of FIG. 6A) and sewn through the cover 32 formed about the stent 24. More preferably, the opposing sides 96a, 96b are stitched into the cover 32 behind the stent 24, and then extended proximally from the prosthetic heart valve 22 as shown. The connector assembly 52, including the housing 60 and the locking element 62, are then assembled as previously described.

Figure 6B:
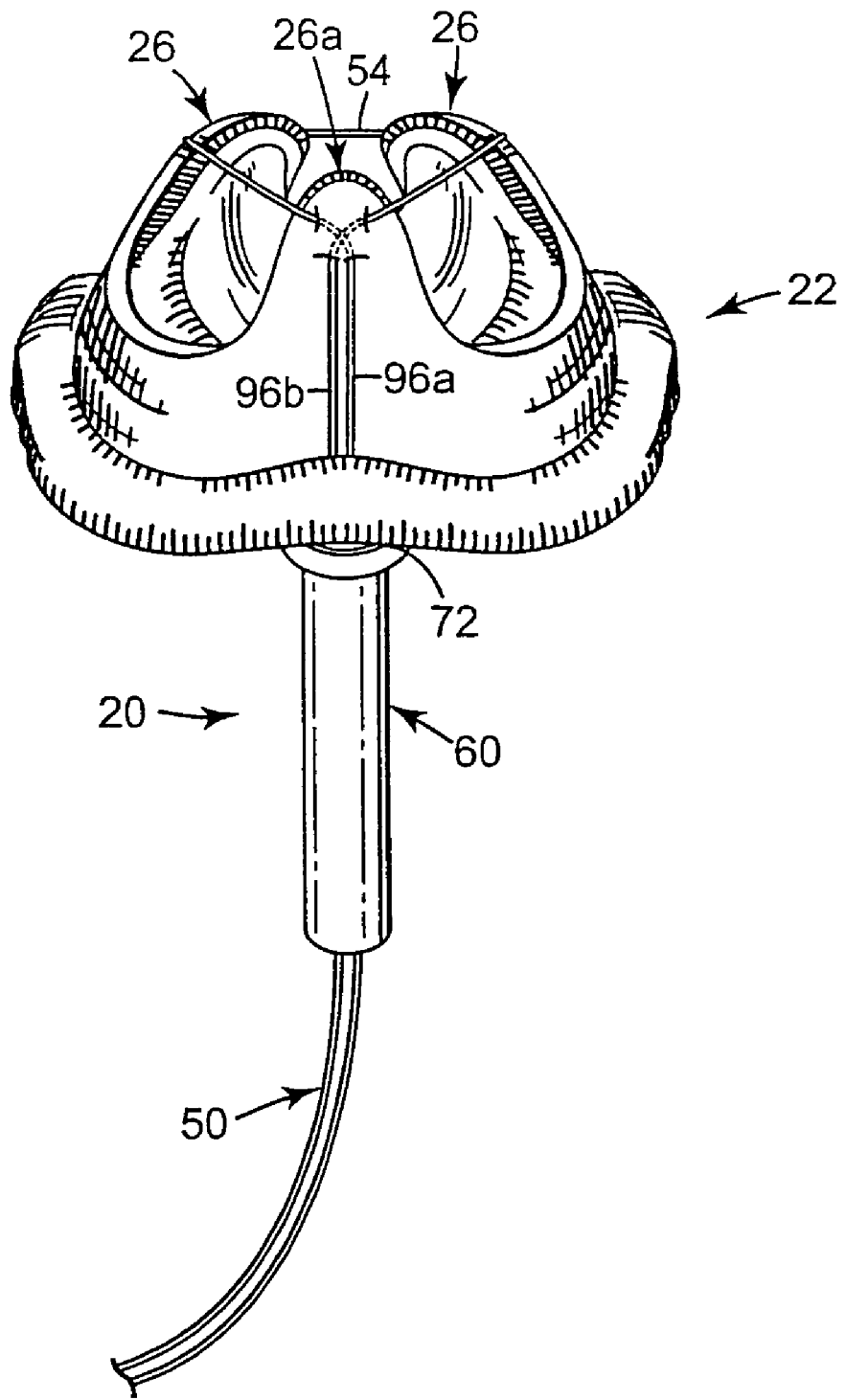

During use, the deflection device 20 is transitioned from the unlocked state of FIG. 6A to the locked state of FIG. 6B in which the stent posts 26 are inwardly deflected. Once again, this transition is achieved by sliding the housing 60 in a distal fashion along the line 50 to a point at which the locking element 62 is "locked" within the housing 60. This action generates a tension in the line 50, shortening a length of the loop 54. In this regard, by extending the opposing sides 96a, 96b of the line 50 through or behind the stent 24, the line 50 is directed away from the patient's anatomy, thereby preventing interference with operation of the connector assembly 52. Further, and in one preferred embodiment, in the tensioning state of FIG. 6B, the distal end 72 of the housing or tensioning component 60 bears against, or is positioned within, the stent 24 such that an entirety of the line 50 extending distal the housing 60 (e.g., the loop 54) does not extend beyond the stent 24 opposite the free ends 38 (i.e., does not extend below the stent 24 relative to the orientation of FIG. 6B).

Figure 7:
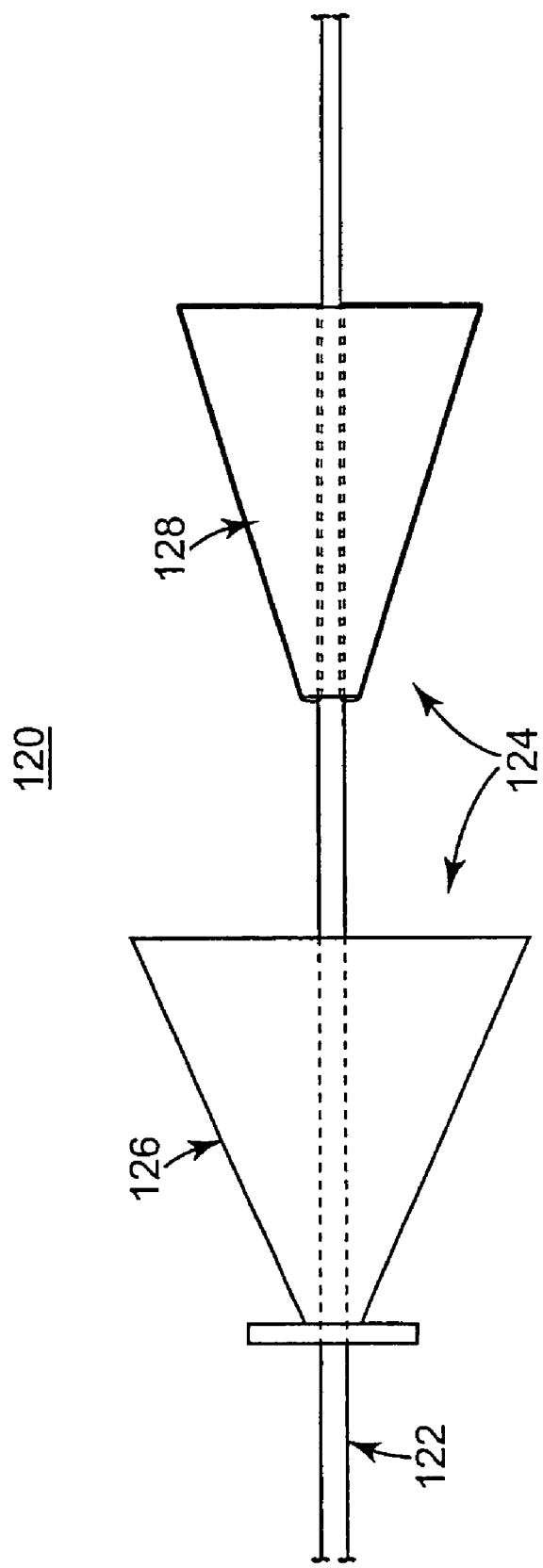
FIG. 7 is a simplified side view of a position of an alternative embodiment deflection device in accordance with the present invention.

The above-described deflection device 20 is but one example of an acceptable device in accordance with the present invention. In this regard, FIG. 7 illustrates an alternative embodiment deflection device 120. For ease of illustration, only a portion of the deflection device 120 is depicted, and is not shown in conjunction with a prosthetic heart valve (such as the prosthetic heart valve 22 of FIG. 1). With this in mind, the deflection device 120 includes a line 122 and a connector assembly 124 (shown partially unassembled in FIG. 7). Similar to previous embodiments, the line 122, upon final assembly to the prosthetic heart valve extends between and interconnects the stent post 26 (FIG. 1). The connector assembly 124 is connected to the line 122 proximal the prosthetic heart valve 22 (i.e., relative to the orientation of FIG. 7, the prosthetic heart valve is to the left of the connector assembly 124), and is transitionable to a locked or tensioning state in which the line 122 is locked in at least one direction relative to the connector assembly 124 and tensions the line 122 to cause inward deflection of the stent posts 26.

With the above in mind, the connector assembly 124 consists of a housing or tensioning component 126 and a locking element 128. As described below, the housing 126 and the locking element 128 are correspondingly configured such that the locking element 128 nests within the housing 126 and is connected to the line 122 so as to allow distal movement of the connector assembly 124 along the line 122 (relative to the prosthetic heart valve 22 (FIG. 1)), yet prevent proximal sliding movement of the connector assembly 124.

Figure 8:
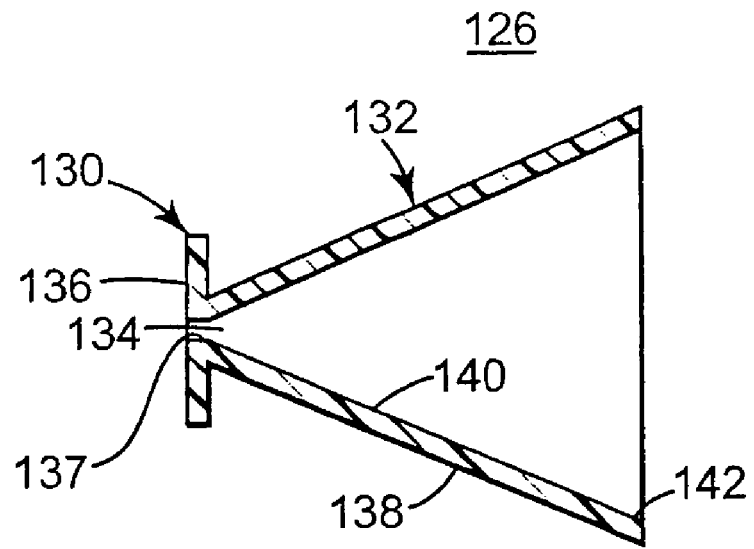
FIG. 8 is a cross-sectional view of a housing portion of the deflection device of FIG. 7.

One preferred embodiment of the housing 126 is illustrated in greater detail in FIG. 8. The housing 126 includes a distal, flange section 130, a proximal, conical section 132, and a central passage 134. The flange section 130 is preferably adapted to provide an outer surface 136 capable of imparting a tension or force on the line 122 (FIG. 7) and/or the stent posts 26 (FIG. 1). Further, the flange section 130 forms an opening 137 for directing the line 122 into the central passage 134.

The conical section 132 is defined by an outer surface 138 and an inner surface 140. In a preferred embodiment, a shape of the inner and outer surfaces 138, 140 is identical, such that both are frusto-conical as shown. Alternatively, the outer surface 138 can assume other shapes conducive to grasping by a surgeon (not shown). To this end, where the outer surface 138 is tapered as shown, the flange section 130 provides an enlarged surface area for conveniently receiving the user's finger(s). Regardless, the inner surface 140 is conical, shaped in accordance with a shape of the locking element 122 (FIG. 7). More particularly, and as described in greater detail below, the inner surface 140 is configured to allow a passage of the locking element 128 into the central passage 134 at a proximal end 142 thereof. Conversely, however, the inner surface 140 tapers to a transverse height less than that of the locking element 128 such that the locking element 128 cannot pass distally beyond the housing 126.

Figure 9:
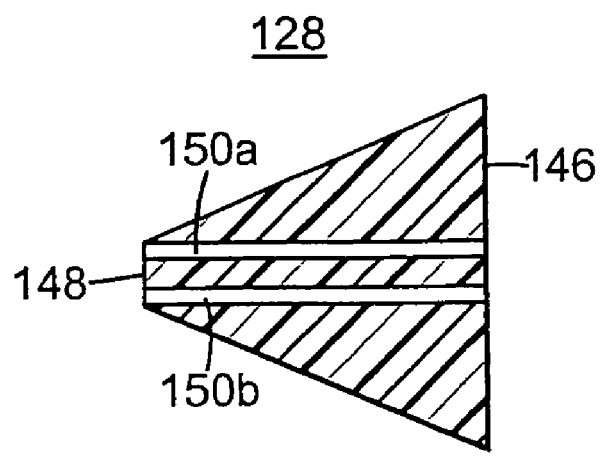
FIG. 9 is a side view of a locking element portion of the deflection device of FIG. 7.

One preferred embodiment of a locking element 128 is illustrated in FIG. 9. The locking element 128 is preferably a conically-shaped bead defining a proximal side 146, a distal side 148, and bores 150a, 150b. The locking element 128 tapers in an outer diameter from the proximal side 146 to the distal side 148, with the so-defined taper corresponding with that of the inner surface 140 (FIG. 8) of the housing 126 (FIG. 8). Further, the bores 150a, 150b extend from the proximal sidewall 146 to the distal side 148. In this regard, the bores 150a, 150b are sized to slidably receive a portion of the line 122 (FIG. 7).

Figure 10:
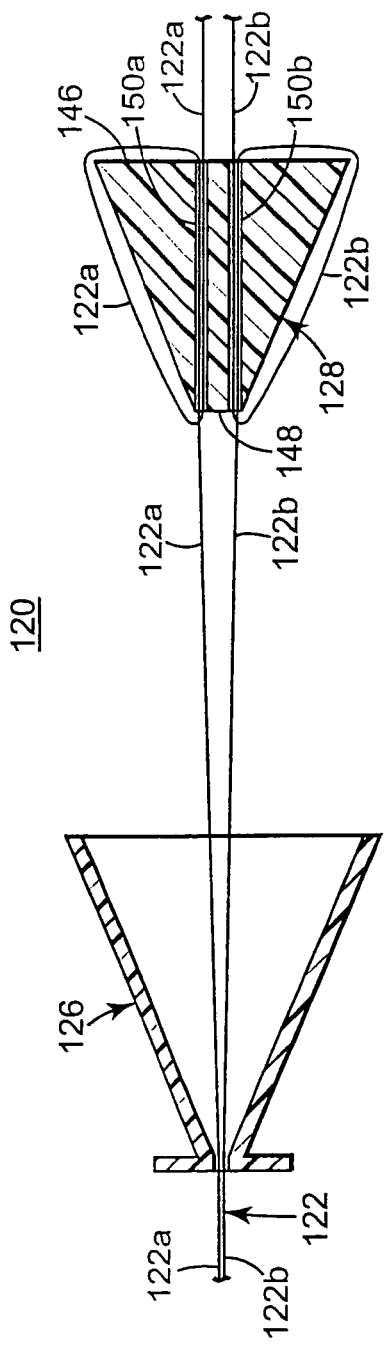
FIG. 10 is a cross-sectional view of the deflection device of FIG. 7 during assembly.

Assembly of the deflection device 120 is illustrated in FIG. 10. The line 122 is connected to the stent posts 26 (FIG. 1) of the prosthetic heart valve 22 (FIG. 1) as previously described such that opposing sides 122a, 122b extend proximally therefrom (i.e., to the right relative to the orientation of FIG. 10). The housing 126 is slid over both of the opposing sides 122a, 122b. The locking element 128 is then connected to the line 122 proximal the housing 126. In particular, the first side 122a is threaded through the bore 150a from the distal side 148 to the proximal side 146. The first side 122a is then wrapped around the locking element 128 to the distal side 148. The first side 122a is again threaded through the bore 150a and extended proximally therefrom. Notably, the first side 122a can be repeatedly wrapped around/through the locking element 128 in a similar fashion where desired. The second side 122b is similarly threaded through the bore 150b and around the locking element 128. Notably, for ease of illustration, the line 122 is illustrated in FIG. 10 as being loose about the locking element 128. Upon final assembly, however, the line 122 is tight against the locking element 128.

Figure 11:
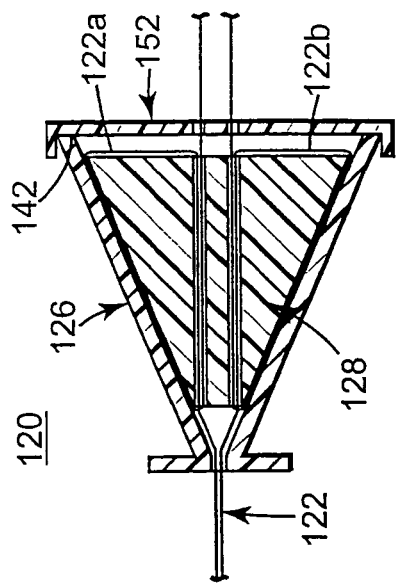
FIG. 11 is a cross-sectional view of the deflection device of FIG. 7 upon final assembly.

The locking element 128 is then slid along the line 122 in a distal fashion and/or the housing 126 is proximally slid along the line 122. Regardless, the locking element 128 is positioned within the central passage 134 of the housing 126 as shown in FIG. 11. In one preferred embodiment, a cap 152 is connected to the proximal end 142 of the housing 126 thereby capturing the locking element 128 within the housing 126.

Upon final assembly, the connector assembly 124 can be slid along the line 122 in a distal fashion (or toward the prosthetic heart valve 22 (FIG. 1) effectuating desired stent post deflection as previously described. Conversely, however, the connector assembly 124 is effectively "locked" to the line 122 relative to possible proximal movement (or away from the prosthetic heart valve 22). In particular, a portion of the line 122 extends between the inner surface 140 of the housing 126 and an exterior of the locking element 128. The distally tapered configuration of these structures allows distal sliding movement to occur, as the line 122 does not become locked between the housing 126 and the locking element 128. Conversely, however, if an attempt is made to slide the housing 26 is a proximal fashion (e.g., by the surgeon or caused by a resistance of the stent posts 26 (FIG. 1) to inward deflection), the housing 126 and the locking element 128 locks against one another, wedging the line 122 therebetween. As a result, the connector assembly 124 cannot be released from the line 122 or otherwise slid in a proximal fashion.

Interface between the housing 126 and the locking element 128 can be further enhanced via alternative configurations. For example, while the cap 152 is provided to capture the locking element 128 relative to the housing 126, the housing 126 can be formed to include a slot, and the locking element 128 formed to include a corresponding projection. With this configuration, the projection of the locking element 128 is engaged within the slot formed by the housing 126, thereby capturing the locking element 128 relative to the housing 126.

Figure 12B:
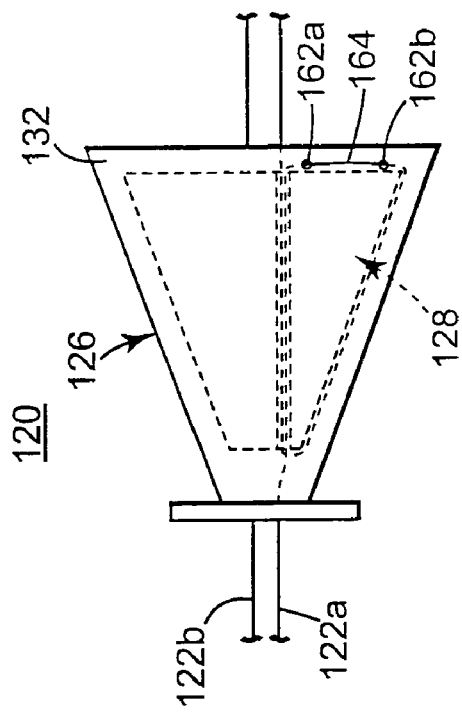
FIG. 12B is a side view of the deflection device of FIG. 7 alternatively modified to promote line release.
Figure 12A:
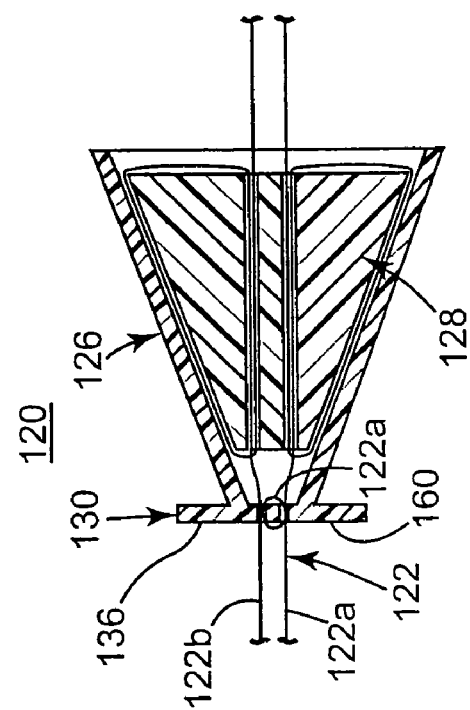
FIG. 12A is a partial perspective view of the deflection device of FIG. 7 modified to promote line release.

As previously described, the deflection device 120 is effectively permanently secured to the line 122. Thus, following implant, the deflection device 120 must be removed from the prosthetic heart valve 22 (FIG. 1). In one embodiment, the line 122 is simply severed distal the connector assembly 124. Alternatively, the connector assembly 124 can be configured to provide a more convenient location for severing of the line 122 at a point further spaced from the prosthetic heart valve 22. For example, as shown in FIG. 12A, the housing 126, and in particular the flange section 130, can include an additional passage 160 through which one of the sides 122a or 122b of the line 122 is threaded. With this configuration, a portion of the line 122 is exposed along the outer surface 136 of the flange 130, and provides a convenient surface for severing the line 122 following implant. Conversely, and with reference to FIG. 12B, the conical section 132 of the housing 126 can include holes 162a, 162b through which one side 122a or 122b of the line 122 is threaded. As a result, a section 164 of the line 122 is exposed adjacent the proximal end 142 of the housing 126. Even further, a notch (not shown) can be placed on the housing 126 at the location of the exposed line 164, further enhancing the ability to cut the line 122 following implant.

Figure 12C:
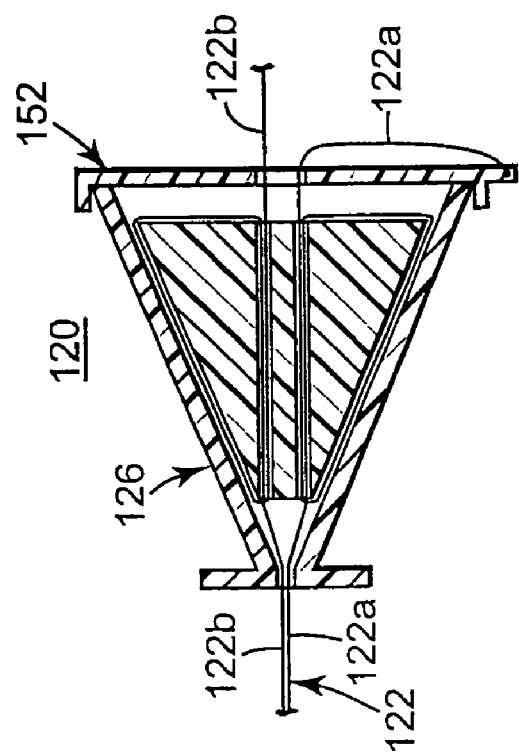
FIG. 12C is a side view of the deflection device of FIG. 7 alternatively modified to promote lien release.

FIG. 12C illustrates another alternative embodiment in which one side 122a of the line 122 is secured to the cap 152. With this configuration, the connector assembly 124 is slid along the line 122 by pulling the other side 122b. Following implant, the first side 122a is exposed relative to the cap 152, and can easily be severed.

Figure 12D:
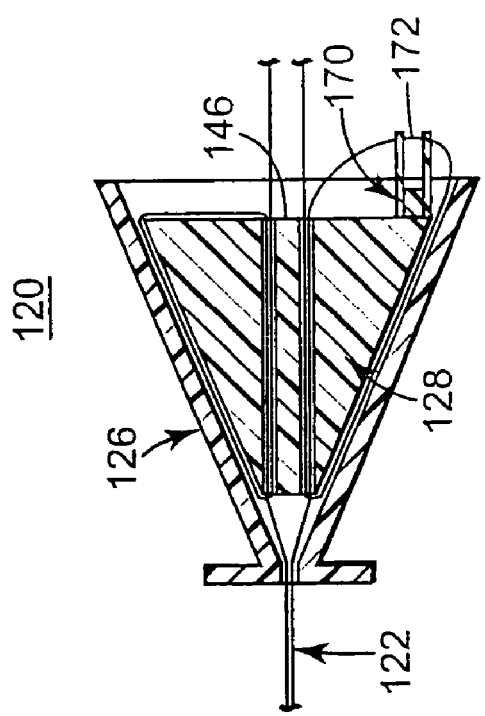
FIG. 12D is a side view of a portion of the deflection device of FIG. 7 alternatively modified to promote line release.

Yet another alternative embodiment is illustrated in FIG. 12D whereby the locking element 128 is formed to include a shoulder 170 extending from the proximal side 146 thereof. The shoulder 170 is adapted to position a section 172 of the line 122 proximal the housing 126 such that following implantation, the line 122 is easily severed at the shoulder 170.

Figure 13:
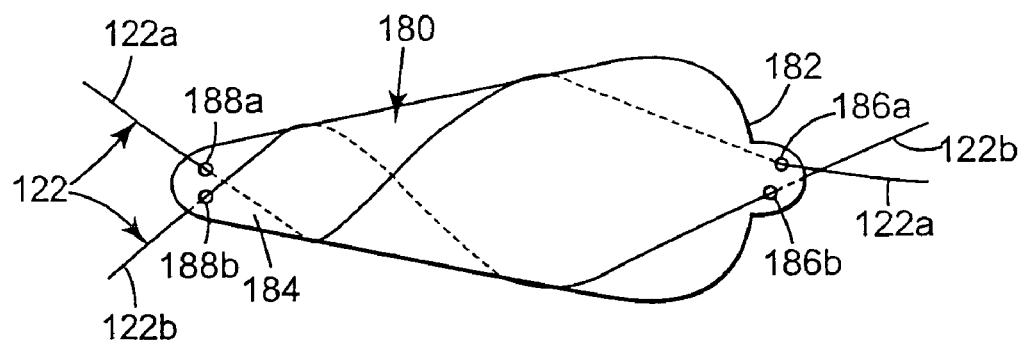
FIG. 13 is a side view of a portion of the deflection device of FIG. 7 alternatively modified to promote line release.

The above-described locking element 128 is but one acceptable configuration. That is to say, the locking element 128 can assume a variety of other shapes, and can be slidably secured to the line 122 in a variety of fashions. For example, FIG. 13 illustrates an alternative embodiment locking element 180 that again defines a proximal side 182 and a distal side 184. The locking element 180 has a generally conical shape, corresponding with that of the housing 126 (FIG. 7), but is adapted to interface with the line 122 along an exterior thereof. In this regard, the proximal side 182 includes two holes 186a, 186b, whereas the distal side 184 includes two holes 188a, 188b. The first side 122a of the line 122 is threaded through the hole 188a at the distal side 184, wrapped about the locking element 180, and then threaded through the hole 186a at the proximal side 182. The second side 122b of the line 122 is similarly threaded through the holes 196b, 188b. With this configuration, the locking element 180 can again slide along the line 122, yet will affect a locked state relative to the housing 126 as previously described.

Figure 14:
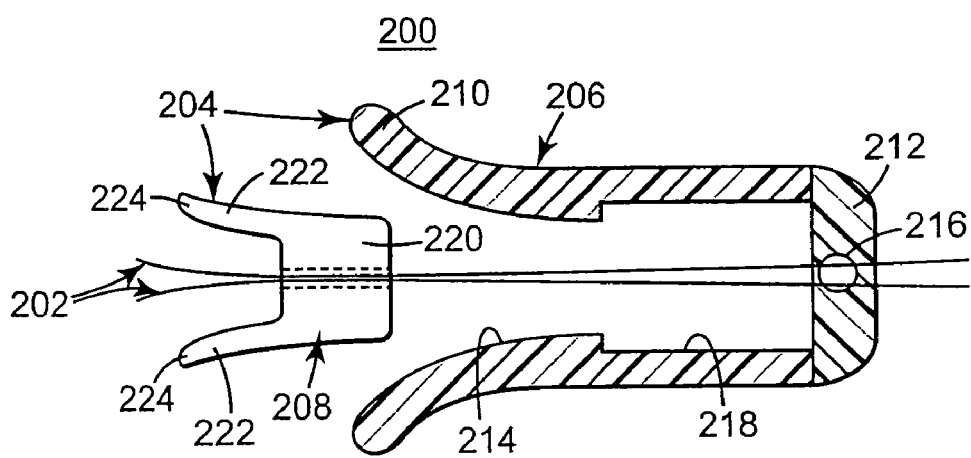
FIG. 14 is a side, cross-sectional view of an alternative embodiment deflection device in accordance with the present invention.

A portion of yet another alternative embodiment deflection device 200 (shown in transverse cross-section) is illustrated in FIG. 14. The deflection device 200 includes a line 202 and a connector assembly 204. For ease of illustration, the deflection device 200 is shown apart from the prosthetic heart valve (shown at 22 in FIG. 1). However, as with previous embodiments, the line 202 is connected to the stent post 26 (FIG. 1) distal the connector assembly 204 (or to the left of FIG. 14). With this orientation in mind, the connector assembly 204 includes a housing or tensioning component 206 and a locking element 208. The locking element 208 is secured to the line 202 as previously described with respect to the deflection device 20 of FIG. 1. The housing 206, in turn, is slidably secured to the line 202 proximal the locking element 208.

With the embodiment of FIG. 14, the housing 206 is highly similar to the housing 60 (FIG. 1) previously described, and includes a distal portion 210, a proximal portion 212, and a central passage 214. The central passage 214 extends from the distal portion 210 to an opening 216 formed in the proximal portion 212. Further, the central passage 214 is sized at the distal portion 210 to receive the locking element 208. Conversely, the opening 216 is sized to be smaller than the locking element 208, such that the locking element 208 cannot pass through the opening 216. Finally, the central passage 214 forms a cavity 218 adjacent the proximal portion 212.

The locking element 208 is preferably an integrally-formed body that defines a head 220 and deflection arms 222. Upon final assembly, the locking element 208 is positioned such that the deflection arms 222 extend distally relative to the head 220 (or toward the prosthetic heart valve 22 (FIG. 1). The head 220 is sized to be received within the central passage 214, including the cavity 218 of the housing 206. The deflection arms 222 further project radially outwardly relative to the head 220, terminating in ends 224. The ends 224 are formed to assume an unbiased outer diameter greater than a diameter defined by the central passage 214 immediately distal the cavity 218. In this regard, the deflection arms 224 are sufficiently flexible to be inwardly deflected, yet resiliently assume the unbiased deflection position shown in FIG. 14. Finally, an axial length of the locking element 208 is sized to approximate, more preferably be slightly less than, an axial length of the cavity 218.

With the above-described configuration in mind, the connector assembly 204 is initially positioned in the unlocked state of FIG. 14, whereby the housing 206 is proximal the locking element 208. The stent posts 26 (FIG. 1) can subsequently be inwardly deflected via the connector assembly 204 by sliding the housing 206 in a distal fashion along the line 202. More particularly, the housing 206 is slid toward the locking element 208 such that the locking element 208 is received within the central passage 214. As the distal portion 210 of the housing 206 extends distally beyond the locking element 208, a tension in the line 202 is generated, causing the stent post deflection as previously described. As the housing 206 is slid over the locking element 208, the deflection arms 222 are biased radially inwardly via interaction with the housing 206. Distal movement of the housing 206 continues until the locking element 208 is within the cavity 218. At this point, an outward radial bias of the deflection arms 222 causes the deflection arms 222 to expand radially outwardly within the cavity 218. More particularly, the ends 224 of the deflection arms 222 deflect radially outwardly to define an outer diameter greater than a diameter of the central passage 214 immediately distal the cavity 218. Effectively, then, the locking element 208 is locked within the housing 206 at the cavity 218. With this configuration, the resulting stent post deflection is maintained until the line 202 is severed.

Figure 15:
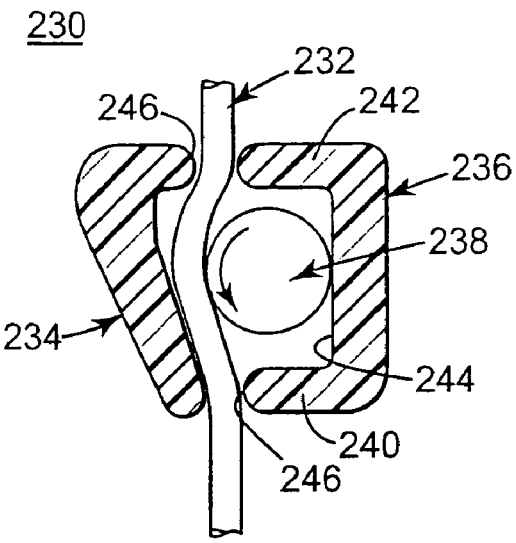
FIGS. 15-17 are cross-sectional views of portions of alternative embodiment deflection devices in accordance with the present invention.

A portion of yet another alternative embodiment deflection device 230 is shown in FIG. 15. The deflection device 230 includes a line 232 and a connector assembly 234. For ease of illustration, the deflection device 230 is shown apart from the prosthetic heart valve 22 (FIG. 1) that would otherwise be connected to the line 232 distal (or below, relative to the orientation of FIG. 15) the connector assembly 234. With this orientation in mind, the connector assembly 234 includes a housing or tensioning device 236 and a locking element 238. In the embodiment of FIG. 15, the housing 236 defines a distal portion 240, a proximal portion 242, and a central passage 244. The distal and proximal portions 240, 242 form openings 246 sized to slidably receive the line 232. The central passage 244 is sized to receive and maintain the locking element 238, and tapers in outer dimension from the proximal portion 242 to the distal portion 240. As shown in FIG. 15, the locking element 238 is circular in cross-section, and is either a cylinder or sphere. Regardless, a cross-sectional height or thickness of the locking element 238 is less than a diameter of the central passage 244 at the proximal portion 242, and greater than a diameter of the opening 246 associated with the distal portion 240. With this configuration, then, the locking element 238 is moveable within the central passage 244, but is prevented from escaping.

During use, the connector assembly 234 can be moved in a distal fashion (or toward the prosthetic heart valve 22 (FIG. 1)), as sufficient clearance is provided between the locking element 238 and the housing 236 adjacent the proximal portion 242 of the central passage 244. Conversely, however, if an attempt is made to move the connector assembly 234 in a proximal fashion (or away from the prosthetic heart valve 22), the locking element 238 is guided, via the line 232, within the central passage 234 toward the distal portion 240. The tapered design of the central passage 244 causes the locking element 238 to lock the line 232 against the housing 236, thereby preventing proximal movement of the connector assembly 234 relative to the line 232.

Figure 16:
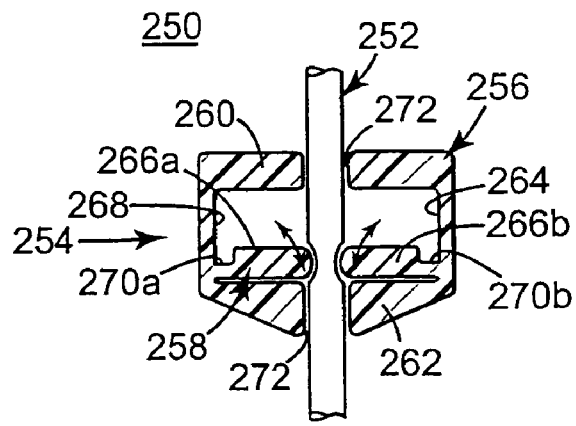

Yet another alternative embodiment deflection device 250 is illustrated in FIG. 16. The deflection device 250 includes a line 252 and a connector assembly 254. For ease of illustration, the deflection device 250 is illustrated apart from the prosthetic heart valve 22 (FIG. 1) that is otherwise connected to the line 252 distal (or below, relative to the orientation of FIG. 16), the connector assembly 254.

With the above orientation in mind, the connector assembly 254 includes a housing or tensioning component 256 forming a locking element 258. In this regard, the housing 256 further defines a proximal portion 260, a distal section 262, and a central passage 264. The locking element 258 is disposed between the distal and proximal portions 260, 262. More particularly, the locking element 258 includes opposing arms 266a, 266b, connected to an inner wall 268 of the housing 256 by a thin section 270a, 270b, respectively. As shown in FIG. 16, the arms 166 extend radially inwardly relative to the housing wall 268. Further, the arms 266a, 266b are positioned in close proximity to the distal portion 260 and longitudinally spaced from the proximal portion 262. Finally, each of the distal and proximal portions 260, 262, forms a hole 272 sized to slidably receive the line 252. With this configuration, the arms 266a, 266b are deflectable or bendable within the central passage 264 toward the proximal portion 262 (or upwardly, relative to the orientation of FIG. 16) via the thin section 270a, 270b. Conversely, however, the arms 266a, 266b are prevented from bending or deflecting distally (or downwardly, relative to the orientation of FIG. 16) due to interaction with the distal portion 260 of the housing 256.

With the above configuration in mind, the line 252 is passed through the housing 256 extending through the holes 272 and between the arms 266. In an undeflected state, a spacing between the arms 266a, 266b is less than a diameter of the line 252. Thus, when undeflected, the arms 266a, 266b "lock" onto the line 252. With this in mind, the housing 256 can be slid along the line 252 in a distal fashion (or toward the prosthetic heart valve 22 (FIG. 1)), as frictional engagement between the arms 266a, 266b and the line 252 causes the arms 266a, 266b to deflect or bend away from the line 252 and toward the proximal portion 266. Proximal movement of the connector assembly 254 along the line 252 (or away from the prosthetic heart valve 22) is prevented because as the line 252 frictionally engages the arms 266a, 266b, the arms 266a, 266b are deflected slightly toward the distal portion 266. Interaction between the distal portion 260 and the arms 266a, 266b prevents overt bending of the arms 266a, 266b to occur. Thus, the line 252 is locked between the arms 266a, 266b.

Figure 17:
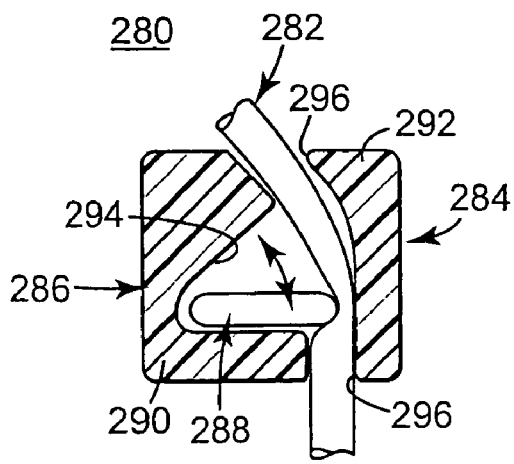

Yet another alternative embodiment deflection device 280 is shown in FIG. 17. The deflection device 280 includes a line 282 and a connector assembly 284. For ease of illustration, the deflection device 280 is shown apart from the prosthetic heart valve 22 (FIG. 1) that is otherwise connected to the line 282 distal (or below, relative to the orientation of FIG. 17) the connector assembly 284.

With the above orientation in mind, the connector assembly 284 includes a housing or tensioning component 286 and a locking element 288. The housing 286 includes a distal portion 290, a proximal portion 292, and a central passage 294. Each of the distal and proximal portions 290 and 292 forms a hole 296 sized to slidably receive the line 282. The central passage 294 extends between the holes 296. More particularly, the central passage 294 tapers in outer diameter from the distal portion 290 to the proximal portion 292. With the embodiment of FIG. 17, the hole 296 associated with the distal portion 290 is formed to be substantially parallel with a central axis of the housing 286, whereas the hole 296 associated with the proximal portion 292 extends at an angle relative to the longitudinal axis.

The locking element 288 is preferably a disc sized to fit within the central portion 294 adjacent the distal portion 290. More particularly, the locking element 288 defines an outer diameter slightly less than an outer diameter of the central passage 294 at the distal portion 290. To this end, a diameter of the locking element 288 is related to a diameter of the central passage portion 294 adjacent the distal portion 290 to define a spacing that is less than a thickness of the line 282. With this configuration, then, the locking element 288 serves to "lock" the line 282 against the housing 286 within the central passage 294 when an attempt is made to slide the connector assembly 284 in a proximal fashion (upwardly relative to FIG. 17 or away from the prosthetic heart valve 22) along the line 282. Conversely, the connector assembly 284 allows for distal movement of the housing 286 along the line 282 (downwardly relative to FIG. 17 or toward the prosthetic heart valve 22), as the line 282 frictionally directs the locking element 288 away from the distal portion 290 and toward the proximal portion 292. In this regard, by preferably forming the hole 296 associated with the proximal portion 292 at an angle, when a subsequent attempt is made to distally slide the housing 286, the line 282 again engages the locking element 288, causing it to pivot to the locked position shown.

Yet another alternative embodiment deflection device 300 is shown in FIG. 18 in conjunction with the prosthetic heart valve 22. The deflection device 300 is highly similar to the deflection device 20 previously described with respect to FIG. 1, and includes a line 302 and a connector assembly 304. The connector assembly 304 includes a housing or tensioning component 306 and a locking element 308. As described below, the locking element 308 is connected to the line 302 and maintains the housing 306.

With the embodiment of FIG. 18, the locking element 308 is a strip or section of tie-back material forming a plurality of angled ridges 310. More particularly, and with additional reference to FIG. 18b, the ridges 310 extend from a base portion 312 and define a slope surface 314 and a locking surface 316. The housing 306 is internally configured to slide over the sloped surface 314 of each ridge 310 when moved in a distal direction (e.g., to the left relative to the orientation of FIGS. 18a and 18b). The locking surface 316 of each ridge 310, in conjunction with an internal configuration of the housing 306, prevents proximal or rearward movement of the housing 306 relative to each ridge 310 once the engaging portion of the housing 306 is moved distal the particular ridge 310. With this configuration, then, the locking element 308 provides a plurality of locked positions, with the housing 306 effectively being locked relative to each ridge 310 once distally moved beyond a particular one of the ridges 310.

During use, the deflection device 300 operates in a manner highly similar to that previously described with respect to FIG. 1. In particular, when inward deflection of the stent post 26 is desired, the housing or tensioning component 306 is moved distally along the locking element 308. More particularly, the housing 306, and in particular, the engagement portion thereof is slid along the slope 314 of consecutive ridges 310 until the housing 306 imparts a tension onto the line 302, thereby inwardly deflecting the free ends 38 of the post 26. Distal movement of the housing 306 continues until a desired inward deflection of the stent post 26 is achieved. Once desired deflection is achieved, the housing 306 is locked relative to the line 302 via engagement with the locking surface 316 of one of the ridges 310.

Figure 19:
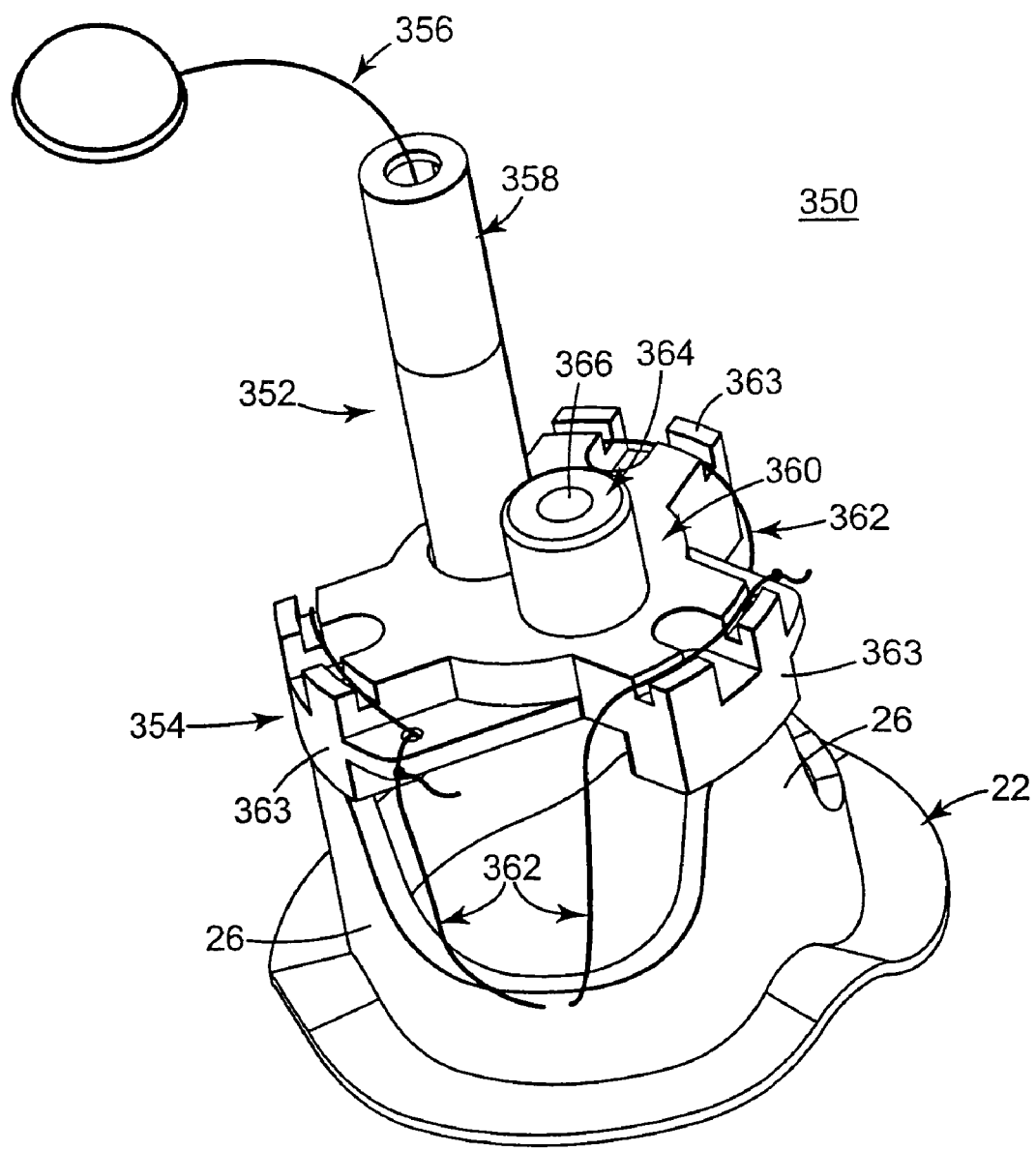
FIG. 19 is an enlarged, perspective view of an alternative embodiment prosthetic heart valve system in accordance with the present invention.

While the deflection device of the present invention has been described as being coupled to the prosthetic heart valve 22 apart from a separate holder component, the prosthetic heart valve system of the present invention can further include such a holder. For example, FIG. 19 illustrates a prosthetic heart valve system 350 including the prosthetic heart valve 22, a deflection device 352, and a holder 354. The deflection device 352 can assume a variety of forms as previously described. With the embodiment of FIG. 19, however, the deflection device 352 is similar to the deflection device 20 previously described with respect to FIG. 1, and thus includes a line 356 and a housing or tensioning component 358. The holder 354 can also assume a variety of forms, but preferably includes a holder body 360 coupled to the prosthetic heart valve 22. In this regard, the holder body 360 is configured to selectively retain the housing 358 of the deflection device 352.

For ease of illustration, connection of the deflection device 352 to the prosthetic heart valve 22, and in particular the stent post 26, is not provided in FIG. 19. In general terms, however, the line 356 extends distally from the housing 358 and passes through/interconnects the stent post 26 at the free ends 38 thereof. Where inward deflection of the stent post 26 is desired, the housing 358 is moved distally along the line 356, tensioning a portion thereof to cause inward deflection of the stent post 26.

The holder 354 is configured to be a prosthetic heart valve 22 apart from coupling of the deflection device 352 to the prosthetic heart valve 22. In this regard, one or more lines (e.g., sutures) 362 selectively couple the holder body 360 to the prosthetic heart valve 22. Regardless, a post 364 extends from the holder body 360 and is adapted to selectively receive a handle (not shown), such as via a threaded bore 366, that otherwise facilitates handling of the prosthetic heart valve 22. Further, the holder body 360 forms an aperture 368 sized to selectively retain the housing 358 as shown in FIG. 19. In this regard, the aperture 68 is preferably open at one end thereof (this opening being hidden in the view of the FIG. 19) such that the housing 358 can be snap-fitted into and out of the aperture 368 as desired.

Upon final assembly, then, the housing 358 is retained by the holder body 360 such that the prosthetic heart valve system 350 can be easily handled. When desired, the housing 358 is removed from the aperture 368 of the holder body 360, and maneuvered to effectuate inward deflection of the stent post 26 as previously described. In this regard, during an implantation procedure, the holder 354 can be removed from the prosthetic heart valve 22 apart from the deflection device 352 by severing the line 362. That is to say, the deflection device 352 can be operated to inwardly deflect the stent post 26, and the holder 354 removed from the prosthetic heart valve 22 while still maintaining inward deflection of the stent post 26 via the deflection device 352.

Figure 20:
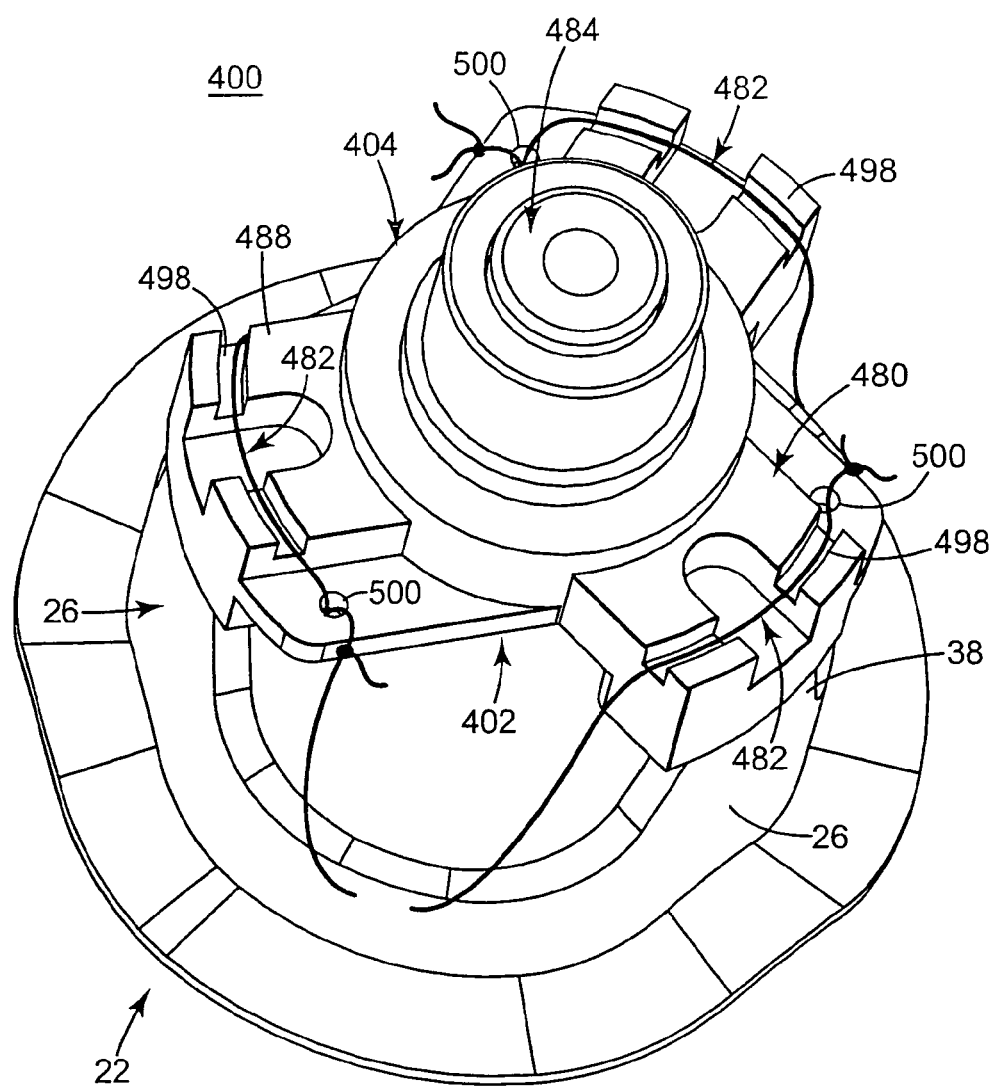
FIG. 20 is an enlarged, perspective view of an alternative embodiment prosthetic heart valve system in accordance with the present invention.

Yet another alternative embodiment prosthetic heart valve system 400 is shown in FIG. 20. The system 400 includes the prosthetic heart valve 22, a deflection device 402 (referenced generally in FIG. 20) and a holder 404. Similar to the embodiment of FIG. 19, the deflection device 402 and the holder 404 are separably coupled to the prosthetic heart valve 22. However, the deflection device 402 represents a slight variation over previous embodiments.

Figure 21A:
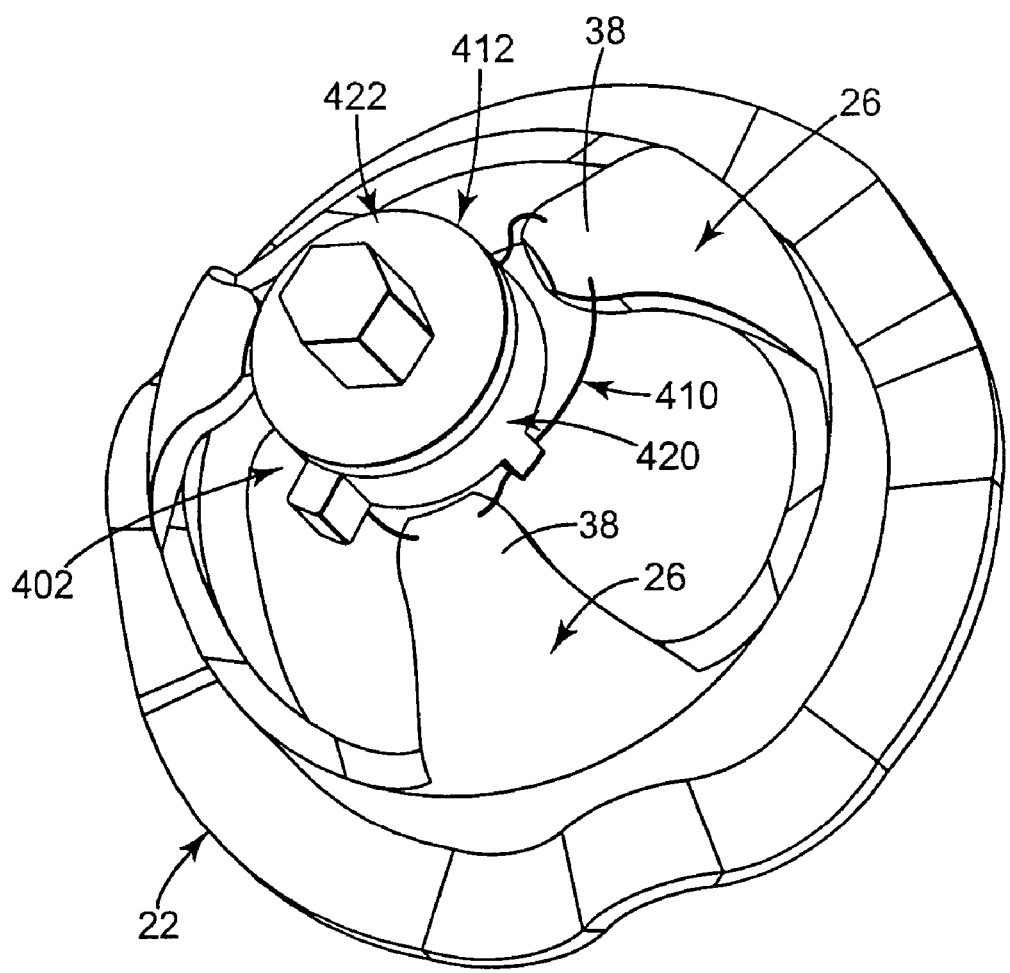
FIG. 21A is an enlarged, perspective view of a deflection device portion of the system of FIG. 20 coupled to a prosthetic heart valve.
Figure 21B:
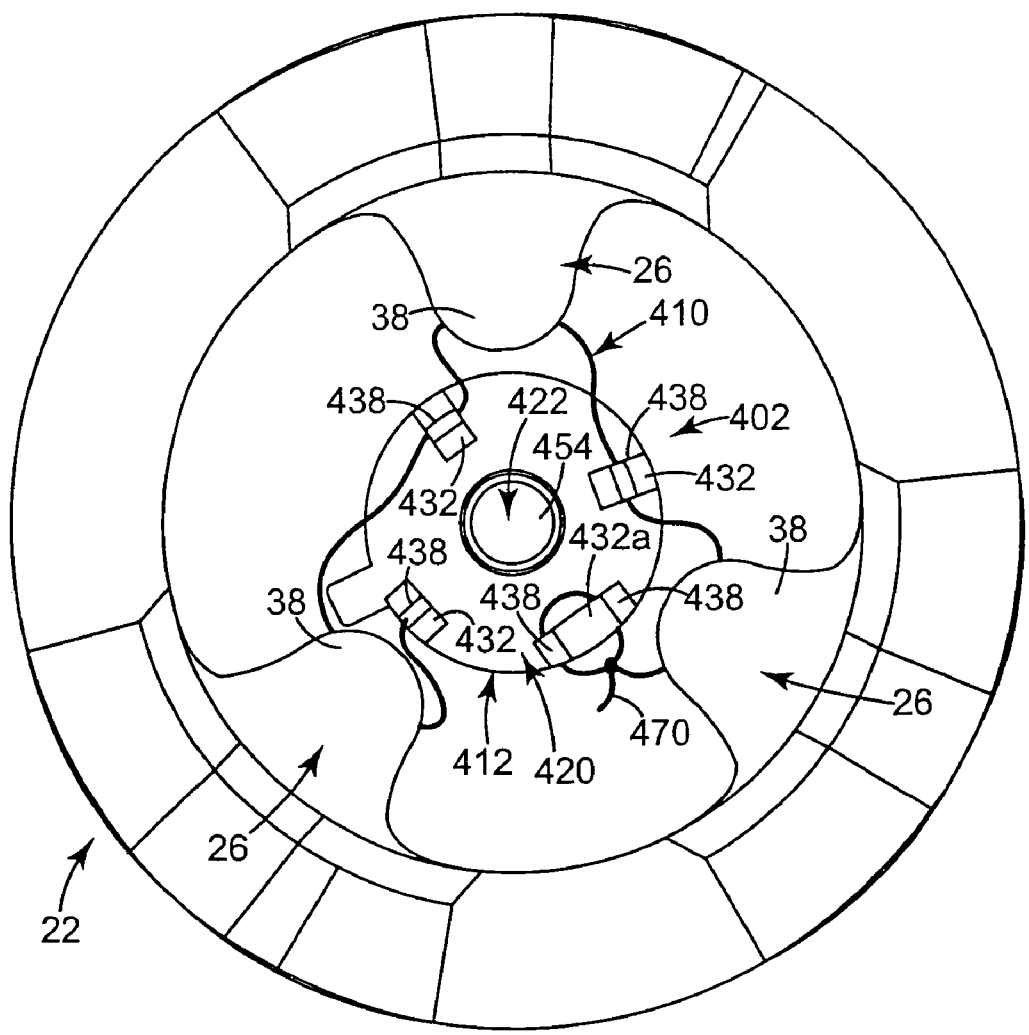
FIG. 21B is a bottom view of the deflection device and prosthetic heart valve of FIG. 21A.

The deflection device 402 is show apart from the holder 404 in FIGS. 21A, 21B. The deflection device 402 generally consists of a line 410 and a tensioning component 412. The line 410 is similar to previous embodiments, and is passed through, and thus interconnects, the free ends 38 of the stent post 26. The tensioning component 412 includes a spool 420 and a ratchet 422. These components are described in greater detail below. In general terms, however, the spool 420 is connected to the line 410. The ratchet 422 is coupled to the spool 420 in a manner such that rotation of the ratchet 422 effectuates rotation of the spool 420, in turn causing the line 410 to be wound around the spool 420 and drawn inward, in turn causing an inward movement or deflection of the free ends 38 of the stent post 26.

Figure 22:
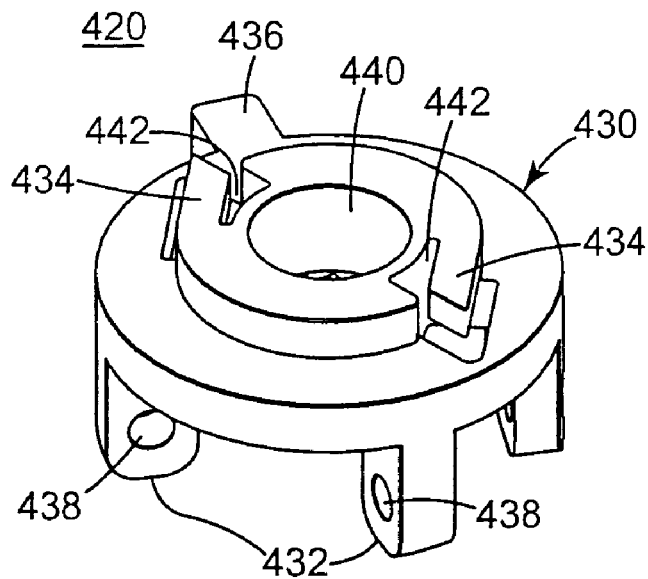
FIG. 22 is a perspective view of a ratchet body portion of the deflection device of FIG. 21A.

The spool 420 is shown in greater detail in FIG. 22 and includes a base 430, a plurality of legs 432, resilient arms 434, and a guide tab 436. Preferably, four of the legs 432 are provided, each extending from the base 430. In this regard, each of the legs 432 forms a passage 438 sized to slidably receive the line 410. In this regard, one of the legs (432a in FIG. 21B) forms two of the passages 438 so as to facilitate securing of the line 410 to the leg 432a as shown. The resilient arms 434 extend in a outward fashion as shown in FIG. 22, and are configured to selectively engage corresponding recesses defined by the ratchet 422 as described below. In this regard, a central opening 440 is defined by the spooling body 420 for receiving a corresponding portion of the ratchet 422. Finally, the guide tab 436 extends in a radial fashion from the base 430, and is adapted for coupling to a corresponding portion of the holder body 404 as described below.

Figure 23:
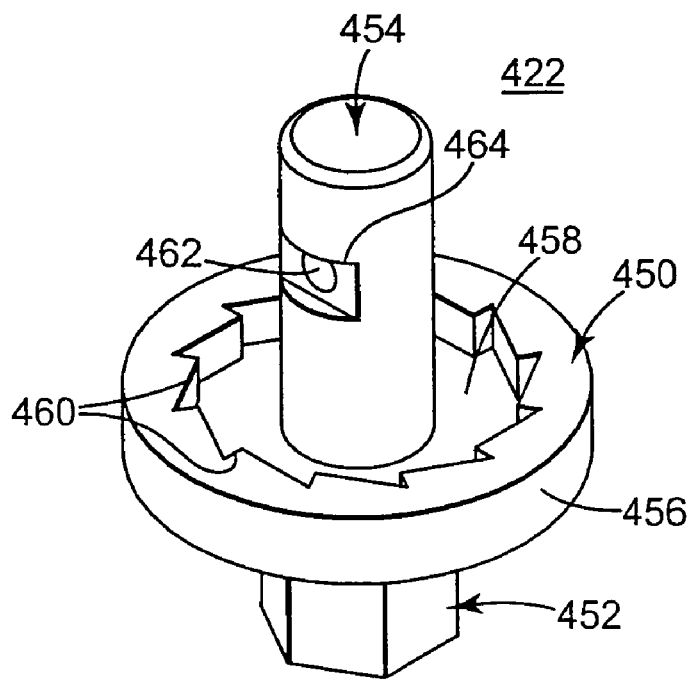
FIG. 23 is a perspective view of a spool body portion of the deflection device of FIG. 21A.

The ratchet body 422 is shown in greater detail in FIG. 23 and includes a platform 450, a post 452, and a shaft 454. The post 452 and the shaft 454 extend in opposite directions from the platform 450.

The platform 450 defines a circular periphery 456 having a diameter corresponding with that of the base 430 (FIG. 22) of the spooling body 420 (FIG. 22). Further, the platform 450 forms a recessed area 458 within which a plurality of teeth 460 are defined. In this regard, the teeth 460 extend in a generally angular fashion as shown, and are configured to selectively engage the resilient arms 434 of the spooling body 420, the combination of which forms a detent or ratchet.

The post 452 is adapted for attachment to a handle component (not shown) in a manner that facilitates rotation of the ratchet body 422. For example, the post 452 preferably defines a hexagonal head that is readily engaged and rotated by a corresponding tool or device. Alternatively, the post 452 can be configured to promote other rotation-facilitating engagement with an auxiliary tool or handle.

The shaft 454 is sized to be received within the central opening 440 of the spooling body 420, and defines a lateral passage 462 sized to receive the line 410 (FIG. 20). In this regard the shaft 454 preferably forms a recess 464 at the lateral passage 462 as shown in FIG. 23. The recess 464 provides a guide area that facilitates winding of the line 410 as described in greater detail below.

The ratchet body 422 is assembled to the spooling body 420 by inserting the shaft 454 of the ratchet body 422 through the central opening 440 of the spooling body 420. The resilient arms 434 nest within the recessed area 458 meshing with respective ones of the teeth 460. In this regard, the slots 442 allow the resilient arms 434 to be compressed radially inwardly, facilitating assertion of the resilient arms 434 within the recessed area 458. After re-expansion of the resilient arms 434, the spooling body 420 is retained relative to the ratchet body 422, with the post 452 and the legs 432 extending in opposite directions.

The above-described deflection device 402 is coupled to the prosthetic heart valve 22 as best shown in FIG. 21B. In particular, the line 410 is secured to the shaft 454 via the lateral passage 462 (best shown in FIG. 23). The line 410 is extended from the shaft 454 and through the passages 438 associated with the legs 432 and the stent post 26 as shown. A leading end 470 of the line 410 is secured to the leg 432a as shown (e.g., a knot is formed). Once assembled, a rotational force placed on the post 452, for example, via a handle device (not shown), causes the ratchet body 422 to rotate, in turn, tensioning the line 410. Interaction between the resilient arms 434 and the teeth 460 prevents unwinding of the line 410. With further rotation of the ratchet body 422, and thus continued winding of the line 410 about the shaft 454, tension is created in the line 410, causing the stent post 26 to inwardly deflect.

Returning to FIG. 20, the holder 404 is configured to be coupled to the prosthetic heart valve 22 apart from the deflection device 402. In this regard, and with additional reference to FIG. 24, the holder 404 includes a holder body 480, a suture 482, and an engagement device 484. The holder body 480 is configured to selectively engage the spooling body 420 (FIG. 22) of the deflection device 402 and includes a central body 486, a plurality of radially extending arms 488, and a guide shaft 490. The central body 486 forms a bore 492 having a diameter approximating that of the base 430 (FIG. 22) of the spooling body 420 (FIG. 22). Further, a groove 494 is formed in the central body 486, sized to receive the tab 436 (FIG. 23) of the spooling body 420. The arms 48 extend radially from the central body 486, each including shoulders 496. The shoulders 496 are configured to selectively receive a corresponding one of the stent post 26. Further, each of the arms 488 defines a slot 498 (best shown in FIG. 20) opposite the shoulder 496, as well as a hole 500. The slot 498 associated with each of the arms 488 is sized to receive one of the sutures 482. Further, the holes 500 are adapted to facilitate securing of one or more of the sutures 42 to the corresponding arm 48. Finally, the guide post 490 defines a passage 502 (partially shown in FIG. 24) that is otherwise aligned with the bore 492 in the central body 486. In this regard, the passage 502 and the bore 492 are sized to receive the sleeve 44 that otherwise forms an engagement surface 504 adapted for coupling to the post 452 (FIG. 23) of the ratchet body 422 (FIG. 23).

Figure 24:
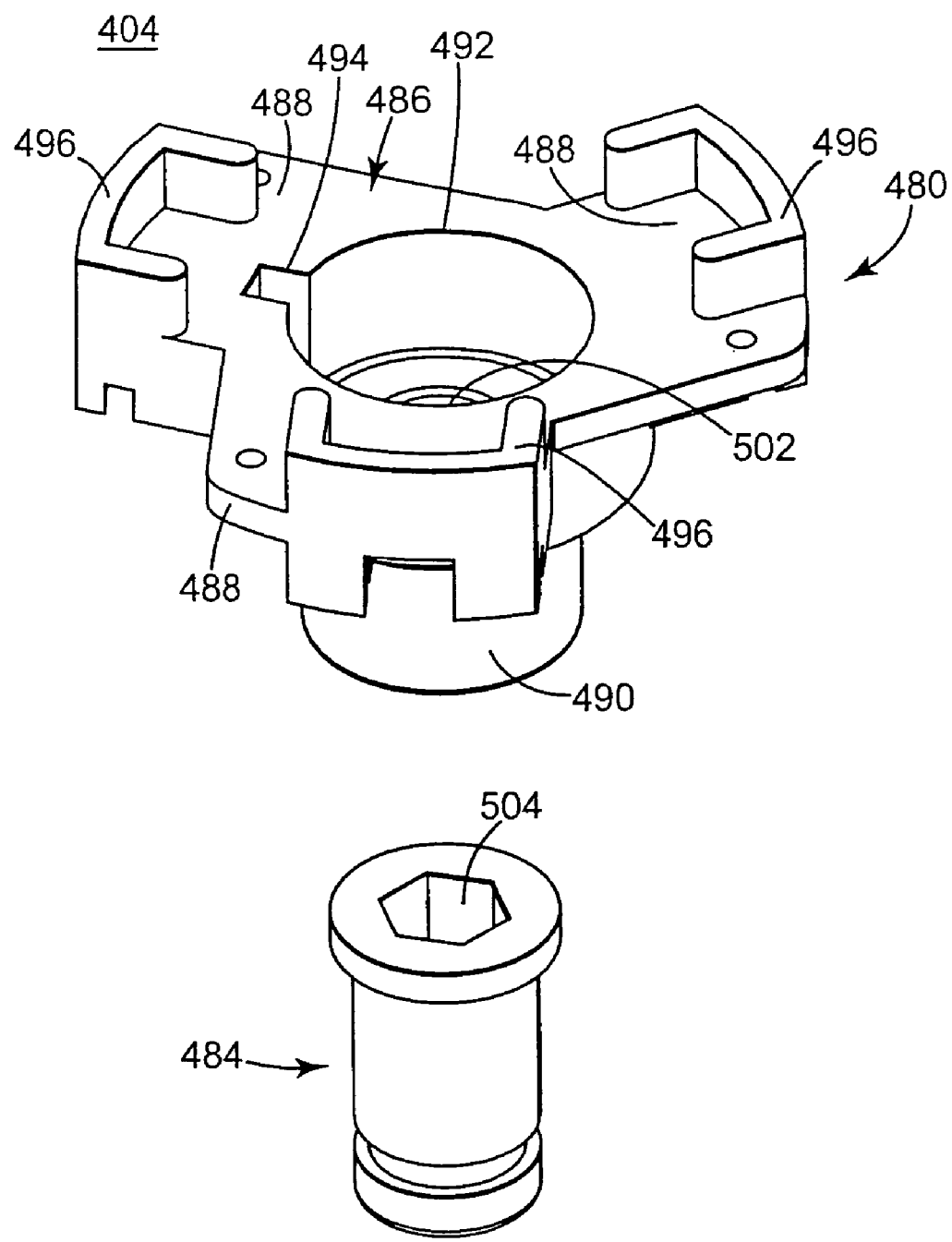
FIG. 24 is an exploded, perspective view of a holder portion of the system of FIG. 20.
Figure 25A:
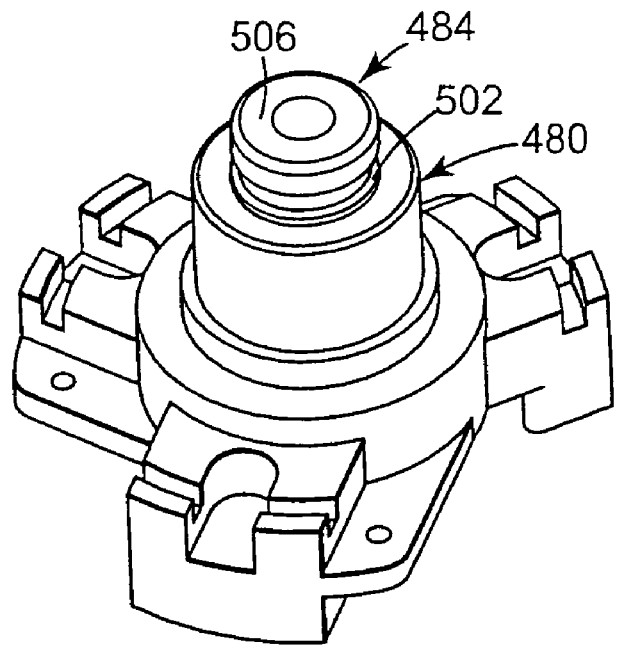
FIGS. 25A and 25B are perspective, assembled views of the deflection device and holder of FIG. 20.
Figure 25B:
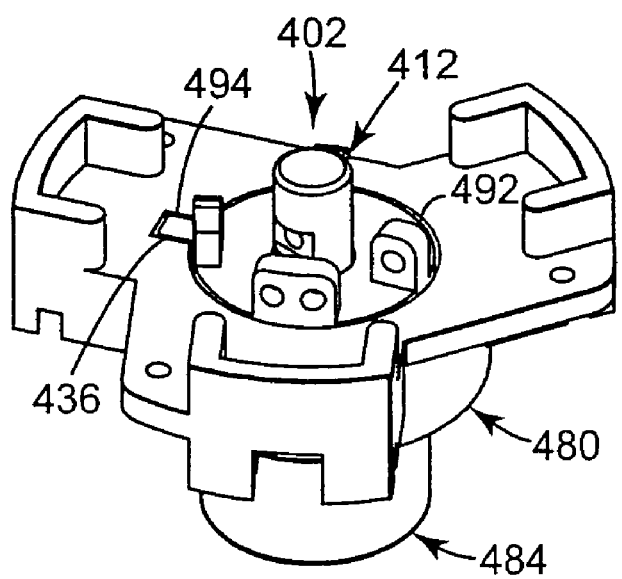

Assembly of the deflection device 402 to the holder 404 is shown in FIGS. 24A and 24B. In particular, the deflection device 402 is slidably received by the holder 404 via the bore 492. The tab 436 nests within the groove 494, thereby preventing rotation of the deflection device 402 relative to the holder 404. The sleeve 44 is positioned within the passage 502, and engages the deflection device 402 via interface between the engagement surface 504 (FIG. 24) and the post 452 (FIG. 23). In one preferred embodiment, a proximal end 506 of the sleeve 44 is adapted for coupling to a handle device (not shown) such as via a threaded bore. Regardless, interface between the sleeve 44 and the post 452 is such that rotation of the sleeve 44 causes rotation of the ratchet body 422 (FIG. 23) as previously described.

Although the present invention has been described with reference to preferred embodiments, workers skilled in the art will recognize that changes can be made in form and detail without departing from the spirit and scope of the present invention.

What is claimed is:

1. A prosthetic heart valve system comprising:
  a prosthetic heart valve including a stent and a plurality of stent posts extending from the stent, each of the stent posts defining a free end; and
  a deflection device for inwardly deflecting the stent post, the deflection device including:
    a line interconnecting and passing through free ends of a plurality of the stent posts,
    a tensioning component that is movably disposed relative to free ends of the stent posts and having an end that is transitional relative to the free ends of the stent posts to a tensioning state in which the end of the tensioning component transitions the line to create tension within the line and thus to inwardly deflect at least one of the stent posts.

2. The prosthetic heart valve system of claim 1, further comprising: a holder having a holder body coupled to the prosthetic heart valve.

3. The prosthetic heart valve system of claim 2, wherein the holder includes a holder body coupled to the prosthetic heart valve, the holder body configured to selectively retain the tensioning component.

4. The prosthetic heart valve system of claim 3, wherein the tensioning component includes a tubular body slidably connected to the line, and further wherein the holder body defines an aperture sized to selectively retain the tubular body.

5. The prosthetic heart valve system of claim 4, wherein the aperture is sized to receive the tubular body via a snap fit.

6. The prosthetic heart valve system of claim 2, wherein the holder body and the tensioning device are separately coupled to the prosthetic heart valve.

7. The prosthetic heart valve system of claim 6, wherein the holder body forms a central passage, and further wherein upon final assembly, the tensioning component is accessible via the central passage.

8. The prosthetic heart valve system of claim 7, wherein the tensioning component includes a rotatable spool including a post, and further wherein upon final assembly, the post is aligned with the central passage.

9. The prosthetic heart valve system of claim 8, wherein the post is engageable with a handle device.

10. The prosthetic heart valve system of claim 8, wherein the connector assembly further includes a ratchet along rotation of the spool only to wind the line around the spool.

11. The prosthetic heart valve system of claim 10, wherein the ratchet is accessible via the central passage.

12. The prosthetic heart valve system of claim 8, wherein the spool includes:
    a base; and
    a plurality of legs extending from the base, each of the legs forming at least one passage sized to slidably receive the line.

13. The prosthetic heart valve system of claim 12, wherein at least one of the legs forms two passages, the two passages sized to slidably receive and facilitate a securing of the line.

14. The prosthetic heart valve system of claim 1, wherein the connector assembly is assembled to the line such that the line defines a loop distal the connector assembly, the loop interconnecting the stent post.

15. The prosthetic heart valve system of claim 14, wherein a length of the loop in a locked state is selected to provide a predetermined amount of inward deflection of the stent post.

16. The prosthetic heart valve system of claim 1, wherein the connector assembly includes:
    a housing defining a proximal end, a distal end, and a central passage, wherein the line is slidably received within the central passage; and
    a locking element secured to the line at a fixed location so as to define a loop in the line adapted to interconnect the stent post;
    wherein the housing and the locking element are configured such that the locking element is slidably receivable within the central passage at the distal end and locks to the housing adjacent the proximal end thereof to define a locked state.

17. The prosthetic heart valve system of claim 16, wherein the distal end of the housing extends distal the locking element in the locked state such that in the locked state, a length of the loop distal the connector assembly is defined by the distal end of the housing.

18. The prosthetic heart valve system of claim 1, wherein the connector assembly further includes a strip of material extending from the line, the strip of material providing a plurality of locking surfaces each adapted to lock the tensioning device relative to the line.

19. The prosthetic heart valve system of claim 1, wherein the prosthetic heart valve is a prosthetic mitral valve.

20. The prosthetic heart valve system of claim 1, wherein the prosthetic heart valve is a prosthetic aortic valve.

21. A prosthetic heart valve system comprising:
    a prosthetic heart valve including a stent and a plurality of stent posts extending from the stent, each of the stent posts defining a free end;
    a holder including a holder body coupled to the prosthetic heart valve; and
    a deflection device including a tensioning component coupled to the prosthetic heart valve apart from the holder body
    wherein the coupling of the holder body and the coupling of the tensioning component are arranged so that upon uncoupling of the holder body from the prosthetic heart valve, the tensioning component remains coupled to the prosthetic heart valve.

22. The prosthetic heart valve system of claim 21, further comprising:
    a first line coupling the holder body to the prosthetic heart valve; and
    a second line coupling the tensioning component to the prosthetic heart valve.

23. The prosthetic heart valve system of claim 21, wherein the system is adapted such that upon uncoupling of the holder body from the prosthetic heart valve, the tensioning component remains coupled to the prosthetic heart valve.

24. The prosthetic heart valve system of claim 21, wherein the tensioning component is selectively maintained by the holder body.

25. The prosthetic heart valve system of claim 24, wherein the tensioning device includes a housing, and further wherein the holder body forms an aperture sized to selectively maintain the housing.

26. The prosthetic heart valve system of claim 21, wherein the holder body and the tensioning device are separately coupled to the prosthetic heart valve.

27. The prosthetic heart valve system of claim 26, wherein the holder body forms a central passage, and further wherein upon final assembly, the tensioning component is accessible via the central passage.

28. The prosthetic heart valve system of claim 27, wherein the tensioning component includes a rotatable spool including a post, and further wherein upon final assembly, the post is aligned with the central passage.

29. The prosthetic heart valve system of claim 28, wherein the post is engageable with a handle device.

30. The prosthetic heart valve system of claim 28, wherein the connector assembly further includes a ratchet along rotation of the spool only to wind the line around the spool.

31. The prosthetic heart valve system of claim 30, wherein the ratchet is accessible via the central passage.

32. The prosthetic heart valve system of claim 21, wherein the prosthetic heart valve is a prosthetic mitral valve.

33. The prosthetic heart valve system of claim 21, wherein the prosthetic heart valve is a prosthetic aortic valve.

34. The prosthetic heart valve system of claim 21, wherein the tensioning component is coupled to the prosthetic heart valve via a line interconnecting the free end of each of the stent posts.

* * * * *